US012154354B2

(12) United States Patent
Galeotti et al.

(10) Patent No.: US 12,154,354 B2
(45) Date of Patent: Nov. 26, 2024

(54) SYSTEM AND METHOD FOR LABELING ULTRASOUND DATA

(71) Applicant: Carnegie Mellon University, Pittsburgh, PA (US)

(72) Inventors: John Galeotti, Pittsburgh, PA (US); Gautam Rajendrakumar Gare, Pittsburgh, PA (US); Jiayuan Li, Shanghai (CN); Ricardo Luis Rodriguez, Baltimore, MD (US)

(73) Assignee: Carnegie Mellon University, Pittsburgh, PA (US)

( * ) Notice: Subject to any disclaimer, the term of this patent is extended or adjusted under 35 U.S.C. 154(b) by 233 days.

(21) Appl. No.: 17/618,163

(22) PCT Filed: Jun. 12, 2020

(86) PCT No.: PCT/US2020/037519
§ 371 (c)(1),
(2) Date: Dec. 10, 2021

(87) PCT Pub. No.: WO2020/252330
PCT Pub. Date: Dec. 17, 2020

(65) Prior Publication Data
US 2022/0262146 A1 Aug. 18, 2022

Related U.S. Application Data

(60) Provisional application No. 62/860,403, filed on Jun. 12, 2019.

(51) Int. Cl.
*G06V 20/70* (2022.01)
*A61B 8/08* (2006.01)
(Continued)

(52) U.S. Cl.
CPC .............. *G06V 20/70* (2022.01); *A61B 8/085* (2013.01); *G06T 3/40* (2013.01); *G06V 10/26* (2022.01);
(Continued)

(58) Field of Classification Search
CPC ........ G06V 20/70; G06V 10/26; G06V 10/82; G06V 2201/03; A61B 8/085; G06T 3/40; G16H 30/40; G16H 50/20
See application file for complete search history.

(56) References Cited

U.S. PATENT DOCUMENTS 7,808,323 B2 10/2010 Takinami et al.
2012/0243757 A1 9/2012 Funka-Lea et al.
(Continued)

FOREIGN PATENT DOCUMENTS

CN 108268870 A 7/2018
CN 109087327 A 12/2018
(Continued)

OTHER PUBLICATIONS

Cheng et al, "Transfer Learning with Convolutional Neural Networks for Classification of Abdominal Ultrasound Images" (published in J Digit Imaging, vol. 30, pp. 234-243, Nov. 2016).*
(Continued)

*Primary Examiner* — Casey L Kretzer
(74) *Attorney, Agent, or Firm* — The Webb Law Firm

(57) ABSTRACT

Provided are methods for labeling ultrasound data. The method may include training a convolutional neural network (CNN) based on ultrasound data. The ultrasound data may include ultrasonic waveform data (e.g., radio frequency (RF) waveform data). An RF input of each downsampling layer of a plurality of downsampling layers in the CNN may be downsampled. The RF input may include RF waveform data for an ultrasound. Tissues in the ultrasound may be seg-
(Continued)

mented based on an output of the CNN. A system is also disclosed.

17 Claims, 10 Drawing Sheets

(51) Int. Cl.
*G06T 3/40* (2024.01)
*G06V 10/26* (2022.01)
*G06V 10/82* (2022.01)
*G16H 30/40* (2018.01)
*G16H 50/20* (2018.01)

(52) U.S. Cl.
CPC .............. *G06V 10/82* (2022.01); *G16H 30/40* (2018.01); *G16H 50/20* (2018.01); *G06V 2201/03* (2022.01)

(56) References Cited

U.S. PATENT DOCUMENTS

| | | | |
|---|---|---|---|
| 2018/0061058 A1 | 3/2018 | Xu et al. | |
| 2019/0008480 A1 | 1/2019 | Gerard et al. | |
| 2019/0130575 A1 | 5/2019 | Chen et al. | |
| 2019/0336107 A1* | 11/2019 | Hope Simpson | ... G01S 15/8977 |
| 2020/0315587 A1* | 10/2020 | Toporek | ............... A61B 8/5269 |
| 2021/0059762 A1* | 3/2021 | Ng | ........................... G06T 7/344 |
| 2021/0265042 A1* | 8/2021 | Kim | ..................... A61B 8/5246 |

FOREIGN PATENT DOCUMENTS

| | | | |
|---|---|---|---|
| WO | 2018127497 A1 | 7/2018 | |
| WO | 2018127498 A1 | 7/2018 | |
| WO | 2018140596 A2 | 8/2018 | |
| WO | 2018209193 A1 | 11/2018 | |

OTHER PUBLICATIONS

Akeret et al., "Radio frequency interference mitigation using deep convolutional neural networks", Astronomy and Computing, 2017, 8 pages.
Badrinarayanan et al., "SegNet: A Deep Convolutional Encoder-Decoder Architecture for Image Segmentation", IEEE transactions on Pattern Analysis and Machine Intelligence, 2017, 14 pages.
Girshick, "Fast R-CNN", Proceedings of the IEEE International Conference on Computer Vision, 2015, pp. 1440-1448.
He et al., "Mask R-CNN", Proceedings of the IEEE International Conference on Computer Vision, 2017, pp. 2961-2969.
Long et al., "Fully Convolutional Networks for Semantic Segmentation", Proceedings of the IEEE International Conference on Computer Vision and Pattern Recognition, 2015, pp. 3431-3440.
Lopata et al., "Performance Evaluation of Methods for Two-Dimensional Displacement and Strain Estimation Using Ultrasound Radio Frequency Data", Ultrasound in Med. & Biol., 2009, pp. 796-812, vol. 35, No. 5.
Nair et al., "Coronary Plaque Classification With Intravascular Ultrasound Radiofrequency Data Analysis", Circulation 106(17), 2002, pp. 2200-2206.
Ren et al., "Faster R-CNN: Towards Real-Time Object Detection with Region Proposal Networks", Advances in Neural Information Processing Systems, 2015, pp. 91-99.
Rodriguez-Granillo et al., "In Vivo Intravascular Ultrasound-Derived Thin-Cap Fibroatheroma Detection Using Ultrasound Radiofrequency Data Analysis", Journal of the American College of Cardiology, 2005, pp. 2038-2042, vol. 46, No. 11.
Ronneberger et al., "U-Net: Convolutional Networks for Biomedical Image Segmentation", International Conference on Medical Image Computing and Computer-Assisted Intervention, 2015, pp. 234-241.
Wagner et al., "Statistical properties of radio-frequency and envelope-detected signals with applications to medical ultrasound", J Opt Soc Am A. 4(5), 1987, pp. 910-922.

* cited by examiner

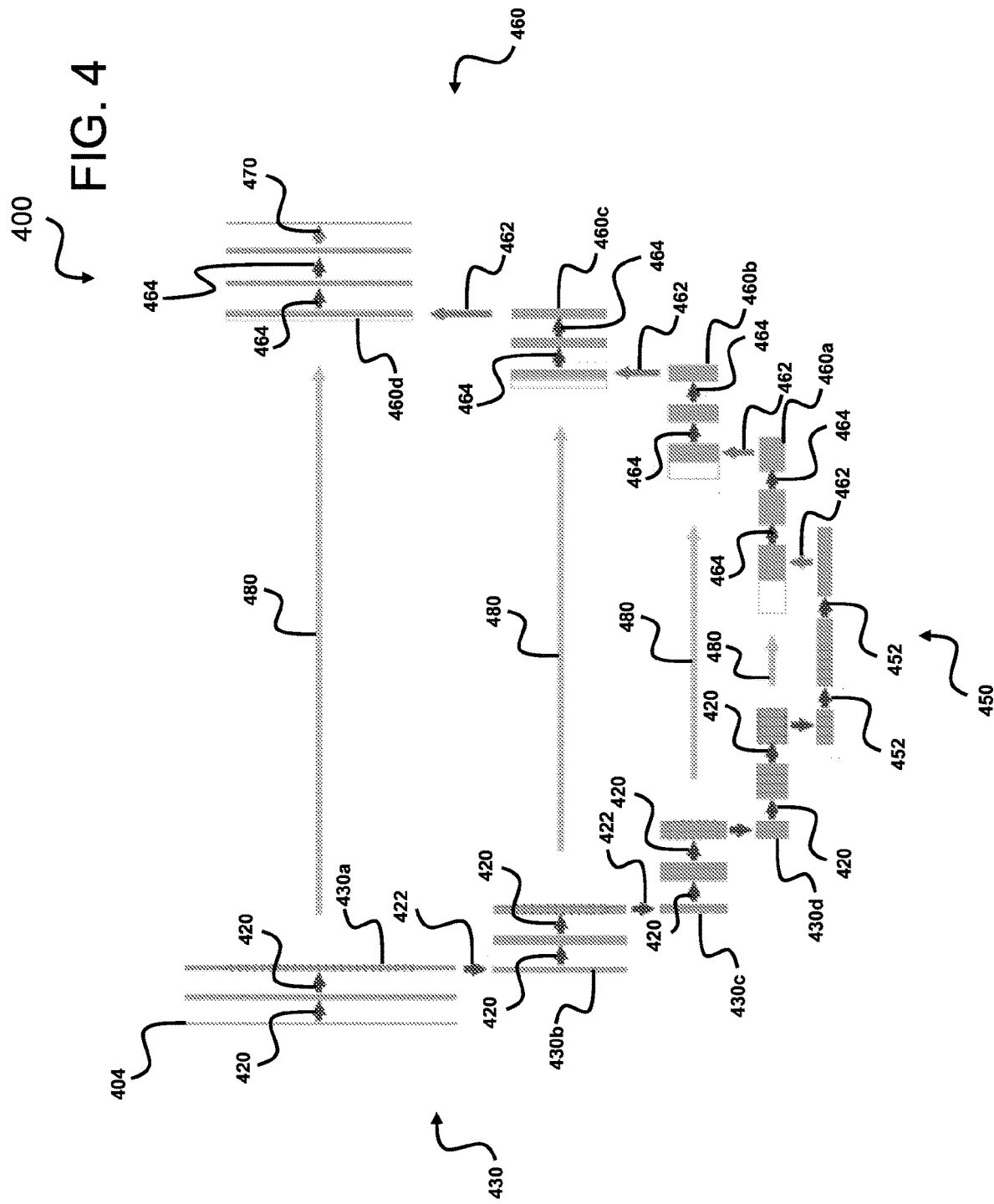

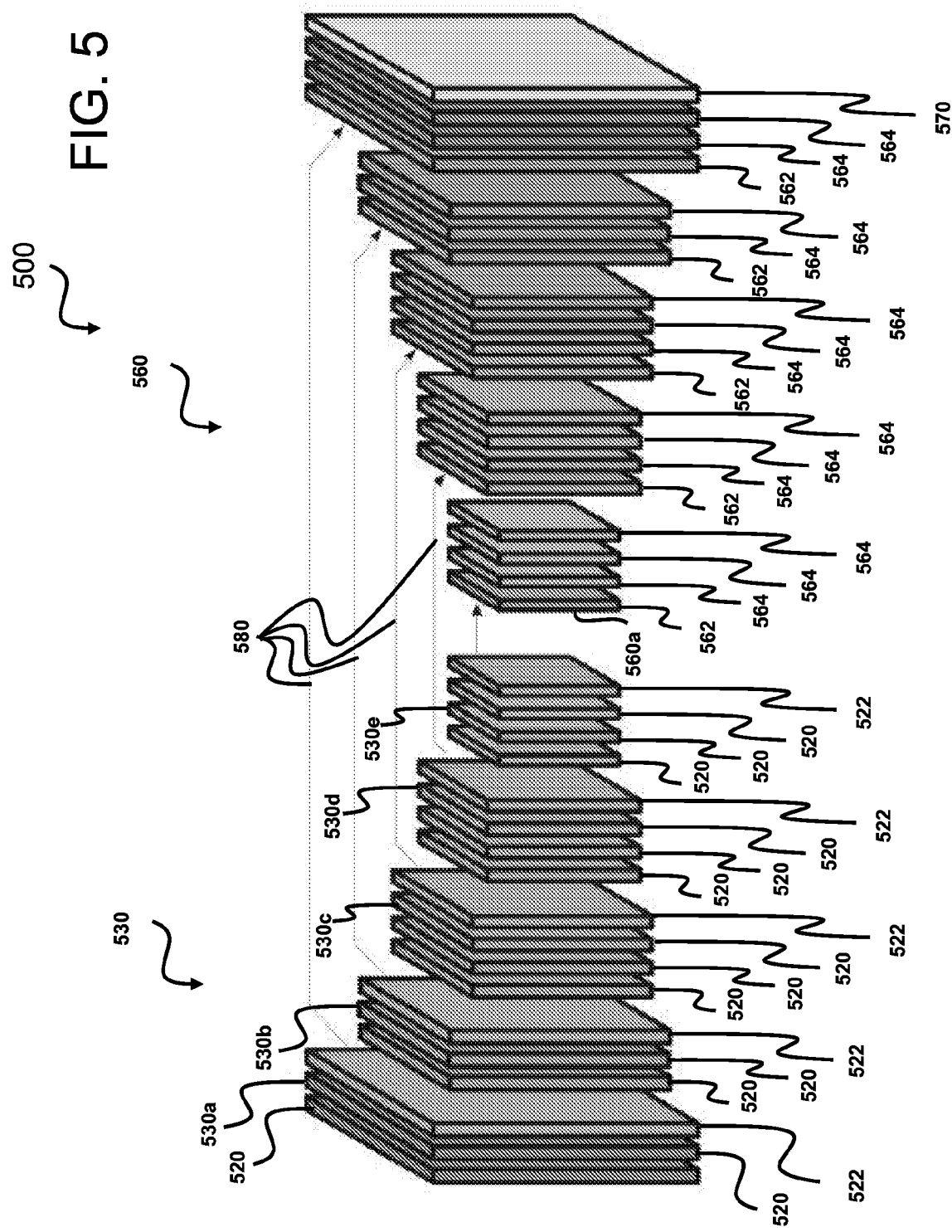

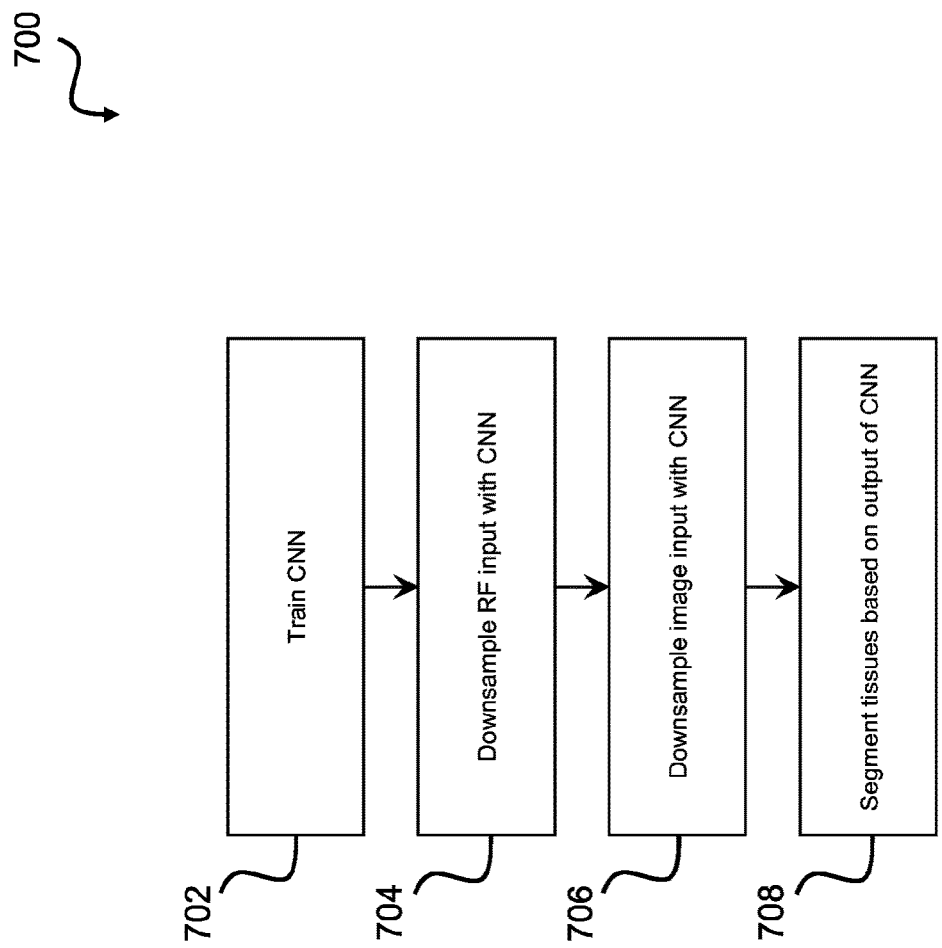

SYSTEM AND METHOD FOR LABELING ULTRASOUND DATA

CROSS-REFERENCE TO RELATED APPLICATIONS

This application is the United States national phase of International Application No. PCT/US2020/037519 filed Jun. 12, 2020, and claims priority to U.S. Provisional Patent Application No. 62/860,403 filed Jun. 12, 2019, the disclosures of which are hereby incorporated by reference in their entirety.

BACKGROUND

1. Field

This disclosure relates generally to ultrasound image processing and, in non-limiting embodiments or aspects, to systems and methods for labeling ultrasound data.

2. Technical Considerations

Ultrasound has become an increasingly popular technique for medical imaging. For example, ultrasound may be relatively low risk (e.g., relatively few potential side-effects and/or the like), relatively inexpensive (e.g., compared to other types of medical image), and/or the like.

However, ultrasound (e.g., ultrasound images and/or the like) may be more challenging to analyze than many other medical imaging modalities because ultrasound pixel values may be dependent on the path through intervening tissue as well as the orientation and properties of the reflective tissue interfaces. As such, even experts with extensive anatomic knowledge may have difficulty drawing precise boundaries between tissue interfaces in ultrasound images, especially when the adjacent tissues have similar acousto-mechanical properties. For example, in shallow subcutaneous tissue, fascia tissue may appear similar to fat tissue in an ultrasound image. Additionally, certain methods for identifying soft tissues in ultrasound images use algorithms that identify specific targets such as vasculature and prostate. Such methods are typically accurate only in constrained limited circumstances and are typically unable to reliably differentiate between several types of tissues.

SUMMARY

According to non-limiting embodiments or aspects, provided is a method for labeling ultrasound data, comprising: training a convolutional neural network (CNN) based on ultrasound data, the ultrasound data comprising ultrasonic waveform data (e.g., radio frequency (RF) waveform data); downsampling an RF input of each downsampling layer of a plurality of downsampling layers in the CNN, the RF input comprising RF waveform data for an ultrasound; and segmenting tissues in the ultrasound based on an output of the CNN.

In non-limiting embodiments or aspects, the method further comprises: downsampling an image input of each downsampling layer of a plurality of downsampling layers in the CNN, the image input comprising a plurality of pixels of the ultrasound. In non-limiting embodiments or aspects, the image inputs and the RF inputs are processed substantially simultaneously. In non-limiting embodiments or aspects, segmenting tissues in the ultrasound comprises labeling a plurality of pixels. In non-limiting embodiments or aspects, the plurality of pixels comprises a majority of pixels in the ultrasound. In non-limiting embodiments or aspects, segmenting tissues comprises identifying at least one of the following: muscle, fascia, fat, grafted fat, skin, tendon, ligament, nerve, vessel, bone, cartilage, needles, surgical instruments, or any combination thereof.

In non-limiting embodiments or aspects, the plurality of downsampling layers comprises an ultrasound image encoding branch and a plurality of RF encoding branches, each RF encoding branch comprising a respective kernel size different than the other RF encoding branches of the plurality of RF encoding branches, the respective kernel size of each RF encoding branch corresponding to a respective wavelength. Additionally or alternatively, each RF encoding branch comprises a plurality of convolution blocks, each convolution block comprising a first convolution layer, a first batch normalization layer, a first activation layer, a second convolution layer, a second batch normalization layer, and a second activation layer, and at least one convolution block of the plurality of convolution blocks comprises a maxpooling layer. Additionally or alternatively, downsampling comprises downsampling the RF input of each RF encoding branch of the plurality of RF encoding branches in the CNN and downsampling an image input of each ultrasound image encoding branch in the CNN, the image input comprising a plurality of pixels of the ultrasound. In non-limiting embodiments or aspects, the method further comprises concatenating an RF encoding branch output of each RF encoding branch and an ultrasound image encoding branch output of the ultrasound image encoding branch to provide a concatenated encoding branch output, and/or upsampling the concatenated encoding branch output with a plurality of upsampling layers in the CNN. In non-limiting embodiments or aspects, the plurality of upsampling layers comprises a decoding branch, the decoding branch comprising a plurality of up-convolution blocks. Additionally or alternatively, the CNN further comprises a plurality of residual connections, each residual connection connecting a respective convolution block of the plurality of convolution blocks to a respective up-convolution block of the plurality of up-convolution blocks having dimensions corresponding to the respective convolution block.

According to non-limiting embodiments or aspects, provided is a system for labeling ultrasound data, comprising at least one computing device programmed or configured to: train a convolutional neural network (CNN) based on ultrasound data, the ultrasound data comprising ultrasonic waveform data (e.g., radio frequency (RF) waveform data); downsample an RF input of each downsampling layer of a plurality of downsampling layers in the CNN, the RF input comprising RF waveform data for an ultrasound; and segment tissues in the ultrasound based on an output of the CNN.

In non-limiting embodiments or aspects, the computing device is further programmed or configured to downsample an image input of each downsampling layer of a plurality of downsampling layers in the CNN, the image input comprising a plurality of pixels of the ultrasound. In non-limiting embodiments or aspects, the image inputs and the RF inputs are processed substantially simultaneously. In non-limiting embodiments or aspects, segmenting tissues in the ultrasound comprises labeling a plurality of pixels. In non-limiting embodiments or aspects, the plurality of pixels comprises a majority of pixels in the ultrasound. In non-limiting embodiments or aspects, segmenting tissues comprises identifying at least one of the following: muscle, fascia, fat, grafted fat, or any combination thereof.

In non-limiting embodiments or aspects, the plurality of downsampling layers comprises an ultrasound image encoding branch and a plurality of RF encoding branches, each RF encoding branch comprising a respective kernel size different than the other RF encoding branches of the plurality of RF encoding branches, the respective kernel size of each RF encoding branch corresponding to a respective wavelength. Additionally or alternatively, each RF encoding branch comprises a plurality of convolution blocks, each convolution block comprising a first convolution layer, a first batch normalization layer, a first activation layer, a second convolution layer, a second batch normalization layer, and a second activation layer, and at least one convolution block of the plurality of convolution blocks comprises a max-pooling layer. Additionally or alternatively, downsampling comprises downsampling the RF input of each RF encoding branch of the plurality of RF encoding branches in the CNN and downsampling an image input of each ultrasound image encoding branch in the CNN, the image input comprising a plurality of pixels of the ultrasound. In non-limiting embodiments or aspects, the computing device is further programmed or configured to concatenate an RF encoding branch output of each RF encoding branch and an ultrasound image encoding branch output of the ultrasound image encoding branch to provide a concatenated encoding branch output and/or upsample the concatenated encoding branch output with a plurality of upsampling layers in the CNN. In non-limiting embodiments or aspects, the plurality of upsampling layers comprises a decoding branch, the decoding branch comprising a plurality of up-convolution blocks. Additionally or alternatively, the CNN further comprises a plurality of residual connections, each residual connection connecting a respective convolution block of the plurality of convolution blocks to a respective up-convolution block of the plurality of up-convolution blocks having dimensions corresponding to the respective convolution block.

According to non-limiting embodiments or aspects, provided is a method for labeling ultrasound data, comprising: receiving an ultrasound image represented by a plurality of pixels; and segmenting the ultrasound image by labeling a majority of pixels of the plurality of pixels.

In non-limiting embodiments or aspects, the majority of pixels are labeled as at least one of the following: muscle, fascia, fat, grafted fat, or any combination thereof. In non-limiting embodiments or aspects, the ultrasound image is segmented based on a convolutional neural network (CNN), further comprising training the CNN based on ultrasound data, wherein at least one input ultrasound image in the ultrasound data comprises fuzzy overlapping labels for a plurality of pixels.

According to non-limiting embodiments or aspects, provided is a system for labeling ultrasound data, comprising at least one computing device programmed or configured to: receive an ultrasound image represented by a plurality of pixels; and segment the ultrasound image by labeling a majority of pixels of the plurality of pixels.

In non-limiting embodiments or aspects, the majority of pixels are labeled as at least one of the following: muscle, fascia, fat, grafted fat, or any combination thereof. In non-limiting embodiments or aspects, the ultrasound image is segmented based on a convolutional neural network (CNN), the computing device further programmed or configured to train the CNN based on ultrasound data, wherein at least one input ultrasound image in the ultrasound data comprises fuzzy overlapping labels for a plurality of pixels.

According to non-limiting embodiments or aspects, provided is a method for labeling ultrasound data, comprising: training an artificial neural network (ANN) based on ultrasound data, the ultrasound data containing ultrasonic waveform data; and segmenting or otherwise labeling tissues in an ultrasound image or video based on an output of the ANN.

In non-limiting embodiments or aspects, the ANN comprises at least one of a convolutional neural network (CNN), a capsule network, a probabilistic network, a recurrent network, a deep network, or any combination thereof. In non-limiting embodiments or aspects, the ultrasonic waveform data comprises at least one of ultrasound images, raw radio frequency (RF) waveform data, beam-formed RF waveform data, an intermediate representation derived from RF waveform data, or any combination thereof. In non-limiting embodiments or aspects, the ultrasonic waveform data or intermediate representation thereof preserves frequency information. In non-limiting embodiments or aspects, the method further comprises at least one of: downsampling an RF input of each downsampling layer of a plurality of downsampling layers in the ANN, the RF input comprising RF waveform data for the ultrasound; or downsampling an image input of each downsampling layer of a plurality of downsampling layers in the ANN, the image input comprising a plurality of pixels of the ultrasound.

Further embodiments or aspects are set forth in the following numbered clauses:

Clause 1. A method for labeling ultrasound data, comprising: training a convolutional neural network (CNN) based on ultrasound data, the ultrasound data comprising radio frequency (RF) waveform data; downsampling an RF input of each downsampling layer of a plurality of downsampling layers in the CNN, the RF input comprising RF waveform data for an ultrasound; and segmenting tissues in the ultrasound based on an output of the CNN.

Clause 2. The method of clause 1, further comprising: downsampling an image input of each downsampling layer of a plurality of downsampling layers in the CNN, the image input comprising a plurality of pixels of the ultrasound.

Clause 3. The method of any preceding clause, wherein the image input and the RF input are processed substantially simultaneously.

Clause 4. The method of any preceding clause, wherein segmenting tissues in the ultrasound comprises labeling a plurality of pixels.

Clause 5. The method of any preceding clause, wherein the plurality of pixels comprises a majority of pixels in the ultrasound.

Clause 6. The method of any preceding clause, wherein segmenting tissues comprises identifying at least one of the following: muscle, fascia, fat, grafted fat, or any combination thereof.

Clause 7. The method of any preceding clause, wherein the plurality of downsampling layers comprises an ultrasound image encoding branch and a plurality of RF encoding branches, each RF encoding branch comprising a respective kernel size different than the other RF encoding branches of the plurality of RF encoding branches, the respective kernel size of each RF encoding branch corresponding to a respective wavelength, wherein each RF encoding branch comprises a plurality of convolution blocks, each convolution block comprising a first convolution layer, a first batch normalization layer, a first activation layer, a second convolution layer, a second batch normalization layer, and a second activation layer, and at least one convolution block of the plurality of convolution blocks comprises a max-pooling layer, and wherein downsampling comprises downsampling the RF input of each RF encoding branch of the plurality of RF encoding branches in the CNN and downsampling an image input of each ultrasound image encoding branch in the CNN, the image input comprising a plurality of pixels of the ultrasound.

Clause 8. The method of any preceding clause, further comprising: concatenating an RF encoding branch output of each RF encoding branch and an ultrasound image encoding branch output of the ultrasound image encoding branch to provide a concatenated encoding branch output; and upsampling the concatenated encoding branch output with a plurality of upsampling layers in the CNN.

Clause 9. The method of any preceding clause, wherein the plurality of upsampling layers comprises a decoding branch, the decoding branch comprising a plurality of up-convolution blocks, wherein the CNN further comprises a plurality of residual connections, each residual connection connecting a respective convolution block of the plurality of convolution blocks to a respective up-convolution block of the plurality of up-convolution blocks having dimensions corresponding to the respective convolution block.

Clause 10. A system for labeling ultrasound data, comprising at least one computing device programmed or configured to: train a convolutional neural network (CNN) based on ultrasound data, the ultrasound data comprising radio frequency (RF) waveform data; downsample an RF input of each downsampling layer of a plurality of downsampling layers in the CNN, the RF input comprising RF waveform data for an ultrasound; and segment tissues in the ultrasound based on an output of the CNN.

Clause 11. The system of clause 10, wherein the computing device is further programmed or configured to downsample an image input of each downsampling layer of a plurality of downsampling layers in the CNN, the image input comprising a plurality of pixels of the ultrasound.

Clause 12. The system of any one of clauses 10-11, wherein the image input and the RF input are processed substantially simultaneously.

Clause 13. The system of any one of clauses 10-12, wherein segmenting tissues in the ultrasound comprises labeling a plurality of pixels.

Clause 14. The system of any one of clauses 10-13, wherein the plurality of pixels comprises a majority of pixels in the ultrasound.

Clause 15. The system of any one of clauses 10-14, wherein segmenting tissues comprises identifying at least one of the following: muscle, fascia, fat, grafted fat, or any combination thereof.

Clause 16. A method for labeling ultrasound data, comprising: receiving an ultrasound image represented by a plurality of pixels; and segmenting the ultrasound image by labeling a majority of pixels of the plurality of pixels.

Clause 17. The method of clause 16, wherein the majority of pixels are labeled as at least one of the following: muscle, fascia, fat, grafted fat, or any combination thereof.

Clause 18. The method of any one of clauses 16-17, wherein the ultrasound image is segmented based on a convolutional neural network (CNN), further comprising training the CNN based on ultrasound data, wherein at least one input ultrasound image in the ultrasound data comprises fuzzy overlapping labels for a plurality of pixels.

Clause 19. A system for labeling ultrasound data, comprising at least one computing device programmed or configured to: receive an ultrasound image represented by a plurality of pixels; and segment the ultrasound image by labeling a majority of pixels of the plurality of pixels.

Clause 20. The system of clause 19, wherein the majority of pixels are labeled as at least one of the following: muscle, fascia, fat, grafted fat, skin, tendon, ligament, nerve, vessel, bone, cartilage, needles, surgical instruments, or any combination thereof.

Clause 21. The system of any one of clauses 19-20, wherein the ultrasound image is segmented based on a convolutional neural network (CNN), the computing device further programmed or configured to train the CNN based on ultrasound data, wherein at least one input ultrasound image in the ultrasound data comprises fuzzy overlapping labels for a plurality of pixels.

Clause 22 A method for labeling ultrasound data, comprising: training an artificial neural network (ANN) based on ultrasound data, the ultrasound data containing ultrasonic waveform data; and segmenting or otherwise labeling tissues in an ultrasound based on an output of the ANN.

Clause 23 The method of clause 22, wherein the ANN comprises at least one of a convolutional neural network (CNN), a capsule network, a probabilistic network, a recurrent network, a deep network, or any combination thereof.

Clause 24. The method of any one of clauses 22-23, wherein the ultrasonic waveform data comprises at least one of ultrasound images, raw radio frequency (RF) waveform data, beam-formed RF waveform data, an intermediate representation derived from RF waveform data, or any combination thereof.

Clause 25. The method of any one of clauses 22-24, wherein the ultrasonic waveform data preserves frequency information.

Clause 26. The method of any one of clauses 22-25, further comprising at least one of downsampling an RF input of each downsampling layer of a plurality of downsampling layers in the ANN, the RF input comprising RF waveform data for the ultrasound; or downsampling an image input of each downsampling layer of a plurality of downsampling layers in the ANN, the image input comprising a plurality of pixels of the ultrasound.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the non-limiting, exemplary embodiments that are illustrated in the accompanying figures, in which:

FIG. 4 illustrates an exemplary implementation of a convolutional neural network according to non-limiting embodiments or aspects;

FIG. 5 illustrates an exemplary implementation of a convolutional neural network according to non-limiting embodiments or aspects;

FIG. 7 is a flow diagram of a method for labeling ultrasound data according to non-limiting embodiments or aspects.

DETAILED DESCRIPTION

Figure 1:
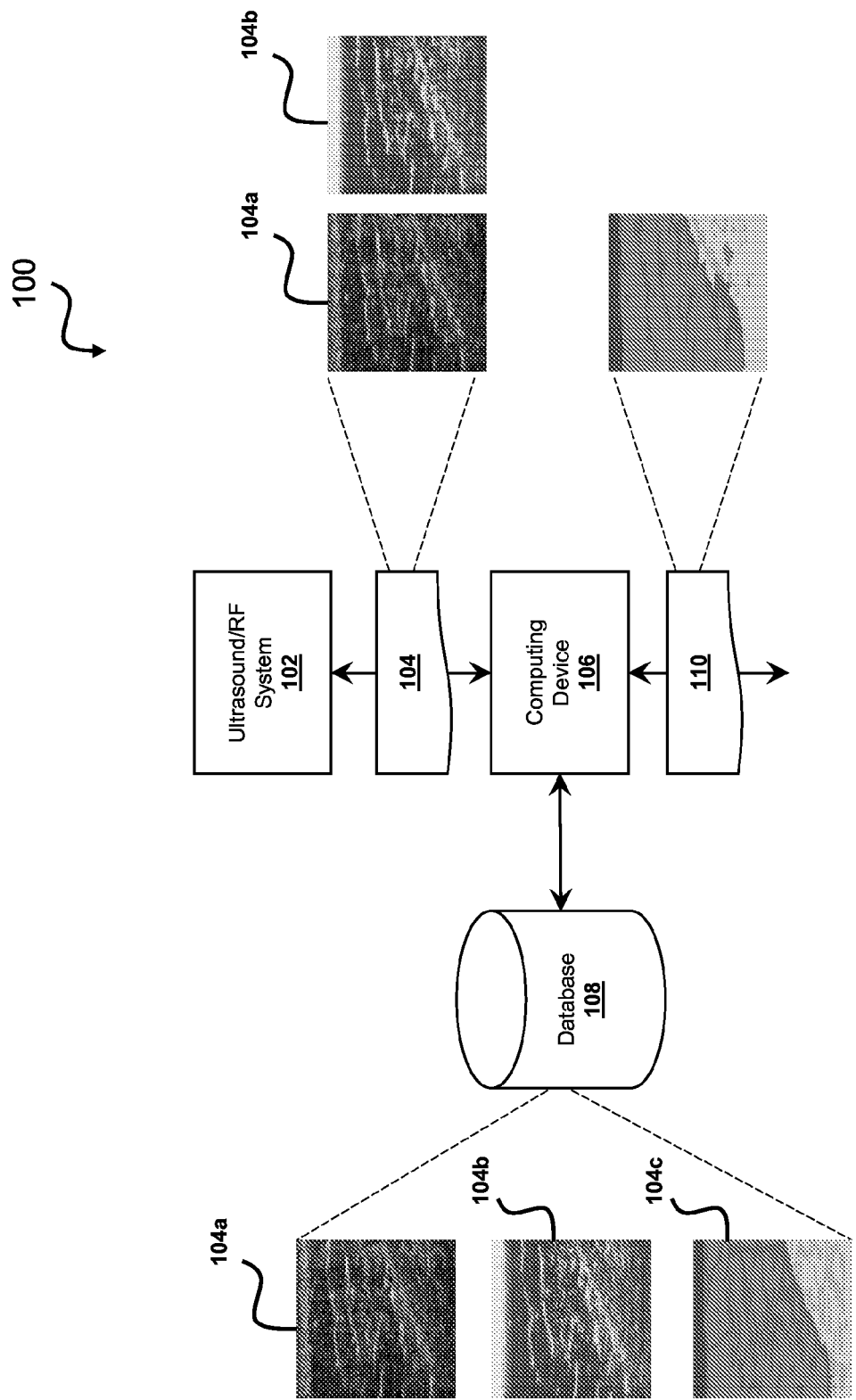
FIG. 1 illustrates a system for labeling ultrasound data according to non-limiting embodiments or aspects.

It is to be understood that the embodiments may assume various alternative variations and step sequences, except where expressly specified to the contrary. It is also to be understood that the specific devices and processes described in the following specification are simply exemplary embodiments or aspects of the disclosure. Hence, specific dimensions and other physical characteristics related to the embodiments or aspects disclosed herein are not to be considered as limiting. No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Also, as used herein, the terms "has," "have," "having," or the like are intended to be open-ended terms. Further, the phrase "based on" is intended to mean "based at least partially on" unless explicitly stated otherwise.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. A computing device may also be a desktop computer or other form of non-mobile computer. In non-limiting embodiments or aspects, a computing device may include an AI accelerator, including an application-specific integrated circuit (ASIC) neural engine such as Apple's "Neural Engine" or Google's Tensor processing unit. In non-limiting embodiments or aspects, a computing device may be comprised of a plurality of individual circuits representing each connection in a neural network, such that each circuit is configured to weigh inputs from each node in a neural network. In such an arrangement, logic gates and/or analog circuitry may be used without needing software, a processor, or memory.

Non-limiting embodiments or aspects provide for a system and method for segmenting ultrasound data using ultrasonic waveform data (e.g., radio frequency (RF) waveform data) of an ultrasound. In non-limiting embodiments or aspects, deep learning computer-vision methodologies are used to automatically identify and label soft tissues visible in ultrasound. Non-limiting embodiments or aspects allow for the differentiation of muscle, fascia, fat, and grafted fat. Non-limiting embodiments or aspects may be applied for plastic surgery operations (e.g., adding or removing fat) and obtaining STEM cells from a patient's fat, including for the treatment of radiation damage from cancer therapy. Muscle, fat, and transplanted fat may appear similar in an ultrasound image, making automatic differentiation very challenging. Non-limiting embodiments or aspects allow for segmenting an ultrasound of shallow subcutaneous tissue (e.g., muscle, fascia, fat, grafted fat, or any combination thereof) using deep learning, e.g., a convolutional neural network (CNN). Non-limiting embodiments or aspects allow for segmenting an ultrasound by labeling a majority of (e.g., all of, substantially all of, and/or the like) pixels in an ultrasound image without the use of a background label. Non-limiting embodiments or aspects enable modifying a CNN to handle image pixels simultaneously with RF waveform data (e.g., for deep learning/CNN segmentation of an ultrasound). In non-limiting embodiments or aspects, a CNN is created such that it can learn RF convolution kernels. Such a configuration may involve handling the differing scale of RF waveforms as compared to image pixel sampling, across both the vertical (e.g., "axial" or RF temporal) and horizontal axes. For example, an encoder-decoder decoder CNN architecture could be modified to have an image (e.g., ultrasound image) downsampling branch (e.g., column, pathway, or set of channels) and at least one parallel RF downsampling branch, with different kernels learned for each RF downsampling branch, as well as multi-channel convolution, which may take the form of a multi-column encoder with late fusion between the ultrasound image branch and RF branch(es). Non-limiting embodiments or aspects provide for a system and method for segmenting ultrasound data using multiple, parallel RF encoding branches that may be incorporated into a CNN. As such, in non-limiting embodiments or aspects, RF waveform data may be processed (e.g., downsampled, etc.) simultaneously with ultrasound image data to improve accuracy and efficiency in segmenting the ultrasound. Non-limiting embodiments or aspects provide for data padding, including novel approaches for padding the deep end of RF waveform data. As such, the same CNN may be used to process ultrasound data (e.g., ultrasound images, RF images, and/or the like) even if certain items of the data are of different sizes (e.g., imaging depth, dimensions, and/or the like).

Non-limiting embodiments may be implemented as software applications used to process ultrasound data output by an ultrasound device. In other non-limiting embodiments, the system and method for labeling ultrasound data may be incorporated directly into an ultrasound device as hardware and/or software.

Referring now to FIG. 1, shown is a system 100 for labeling ultrasound data according to non-limiting embodiments or aspects. The system 100 may include ultrasound/RF system 102. For example, ultrasound/RF system 102 may include an ultrasound device configured to physically capture ultrasonic waveform data (e.g., RF waveform data). In non-limiting embodiments or aspects, ultrasound/RF system 102 may preserve (e.g., store, communicate, and/or the like) only certain data associated with the RF waveform data (e.g., the RF waveform's amplitude envelope and/or the like), which may be used to create a greyscale ultrasound image. For example, raw, per-element RF waveforms may be combined into beam-formed RF waveforms, and the envelopes of the beam-formed RF waveforms may form the basis of the greyscale ultrasound images (e.g., for display on a screen and/or the like). Additionally or alternatively, the frequency content may be used by ultrasound/RF system 102 to compute Doppler-shifts to measure velocities (e.g., which may be displayed in color). In non-limiting embodiments or aspects, the original RF waveform data may be discarded after certain data (e.g., envelope, Doppler-shift, and/or the like) have been computed (e.g., derived, determined, and/or the like). Additionally or alternatively, ultrasound/RF system 102 may preserve the RF waveform data for additional analysis (e.g., save, analyze, and/or the like RF waveform data). In non-limiting embodiments or aspects, ultrasound/RF system 102 may include an ultrasound device that captures and preserves RF waveform data (e.g., beam-formed RF waveform data, per-element RF waveform data, any other suitable representation of the RF waveform (e.g., that preserves frequency content), any combination thereof, and/or the like). Additionally or alternatively, the RF waveform data may be used in real-time for on-line analysis, may be saved for later analysis, any combination thereof, and/or the like. In non-limiting embodiments or aspects, ultrasound/RF system 102 may include a portable ultrasound machine, such as a crystal-linear array scanner and/or the like. For example, ultrasound/RF system 102 may include a Clarius L7 portable ultrasound machine. In non-limiting embodiments or aspects, ultrasound/RF system 102 may be used to obtain at least one ultrasound image 104a (e.g., a greyscale image and/or the like), RF waveform data 104b (e.g., at least one RF image, a set of RF waveforms, and/or the like, which may that correspond to 104a), any combination thereof, and/or the like from at least one patient. For example, a clinician may use ultrasound/RF system 102 to obtain such images. Additionally or alternatively, ultrasound/RF system 102 may output (e.g., communicate and/or the like) ultrasound data 104, which may include at least one ultrasound image 104a, RF waveform data 104b, any combination thereof, and/or the like. In non-limiting embodiments or aspects, ultrasound/RF system 102 may include one or more devices capable of receiving information from and/or communicating information to computing device 106, database 108, and/or the like.

Computing device 106 may include one or more devices capable of receiving information from and/or communicating information to ultrasound system/RF system 102, database 108, and/or the like. In non-limiting embodiments or aspects, computing device 106 may implement at least one convolutional neural network (e.g., W-Net, U-Net, AU-Net, SegNet, any combination thereof, and/or the like), as described herein. In non-limiting embodiments or aspects, computing device 106 may receive ultrasound data 104 (e.g., ultrasound image 104a, RF waveform data 104b, any combination thereof, and/or the like) from ultrasound/RF system 102. Additionally or alternatively, computing device 106 may receive (e.g., retrieve and/or the like) ultrasound data 104 (e.g., historical ultrasound data, which may include at least one ultrasound image 104a, RF waveform data 104b, at least one labeled ultrasound image 104c, any combination thereof, and/or the like, as described herein) from database 108.

In non-limiting embodiments or aspects, computing device 106 may train the CNN based on ultrasound data 104, as described herein. Additionally or alternatively, computing device 106 may downsample ultrasound data 104 (e.g., RF waveform data 104b, ultrasound image 104a, any combination thereof, and/or the like) with the CNN implemented by computing device 106, as described herein. For example, computing device 106 may downsample an RF input (e.g., RF waveform data 104b for an ultrasound and/or the like) of each downsampling layer of a plurality of downsampling layers in the CNN, as described herein. Additionally or alternatively, computing device 106 may downsample an image input (e.g., at least one ultrasound image 104a comprising a plurality of pixels of the ultrasound) of each downsampling layer of a plurality of downsampling layers in the CNN, as described herein. In non-limiting embodiments or aspects, the image inputs (e.g., ultrasound image(s) 104a and/or the like) and the RF inputs (e.g., RF waveform data 104b) may be processed substantially simultaneously (e.g., via parallel branches of the CNN, as separate channels of an input image to the CNN, any combination thereof, and/or the like), as described herein. In non-limiting embodiments or aspects, computing device 106 may segment tissues in the ultrasound based on an output of the CNN, as described herein. For example, segmenting tissues in the ultrasound may include labeling a plurality of pixels (e.g., a majority of pixels, all pixels, and/or the like) in the ultrasound, as described herein. Additionally or alternatively, segmenting tissues (e.g., labeling pixels and/or the like) may include identifying at least one of the following: muscle, fascia, fat, grafted fat, skin, tendon, ligament, nerve, vessel, bone, cartilage, needles, surgical instruments, any combination thereof, and/or the like, as described herein. In non-limiting embodiments or aspects, computing device 106 may output segmented ultrasound data 110 (e.g., segmented ultrasound images and/or the like), as described herein.

In non-limiting embodiments or aspects, computing device 106 may be separate from ultrasound/RF system 102. Additionally or alternatively, computing device 106 may be incorporated (e.g., completely, partially, and/or the like) into ultrasound/RF system 102.

Database 108 may include one or more devices capable of receiving information from and/or communicating information to ultrasound/RF system 102, computing device 106, and/or the like. In non-limiting embodiments or aspects, database 108 may store ultrasound data 104 (e.g., historical ultrasound data) from previous ultrasound/RF scans (e.g., by ultrasound/RF system 102, other ultrasound and/or RF systems, and/or the like). For example, the (historical) ultrasound data 104 may include at least one ultrasound image 104a, RF waveform data 104b, at least one labeled ultrasound image 104c, any combination thereof, and/or the like, as described herein. In non-limiting embodiments or aspects, a clinician may provide labels for labeled ultrasound image(s) 104c. Additionally or alternatively, such labeled ultrasound image 104c may be used for training and/or testing the CNN (e.g., to determine how accurately the segmented tissues based on the outputs of the CNN correspond to the labels provided by the clinician and/or the like), as described herein.

In non-limiting embodiments or aspects, database 108 may be separate from computing device 106. Additionally or alternatively, database may be implemented (e.g., completely, partially, and/or the like) by computing device 106.

In non-limiting embodiments or aspects, ultrasound/RF system 102, computing device 106, and database 108 may be implemented (e.g., completely, partially, and/or the like) by a single device, a single system, and/or the like.

Figure 2:
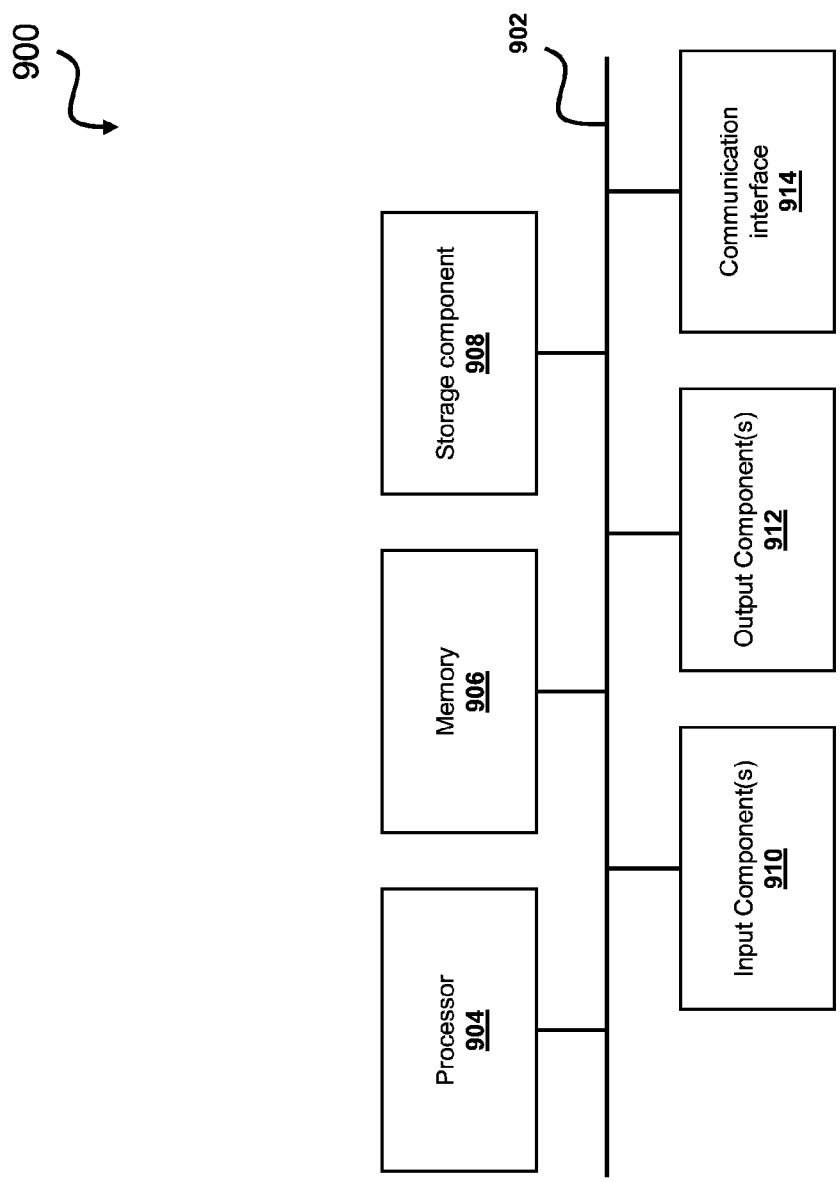
FIG. 2 illustrates example components of a computing device used in connection with non-limiting embodiments or aspects.

Referring now to FIG. 2, shown is a diagram of example components of a computing device 900 for implementing and performing the systems and methods described herein according to non-limiting embodiments. In non-limiting embodiments or aspects, device 900 may include additional components, fewer components, different components, or differently arranged components than those shown in FIG. 2. Device 900 may include a bus 902, a processor 904, memory 906, a storage component 908, an input component 910, an output component 912, and a communication interface 914. Bus 902 may include a component that permits communication among the components of device 900. In non-limiting embodiments or aspects, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read-only memory (ROM), and/or another type of dynamic or static storage device (e.g., flash memory, magnetic memory, optical memory, etc.) that stores information and/or instructions for use by processor 904.

With continued reference to FIG. 2, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Figure 3:
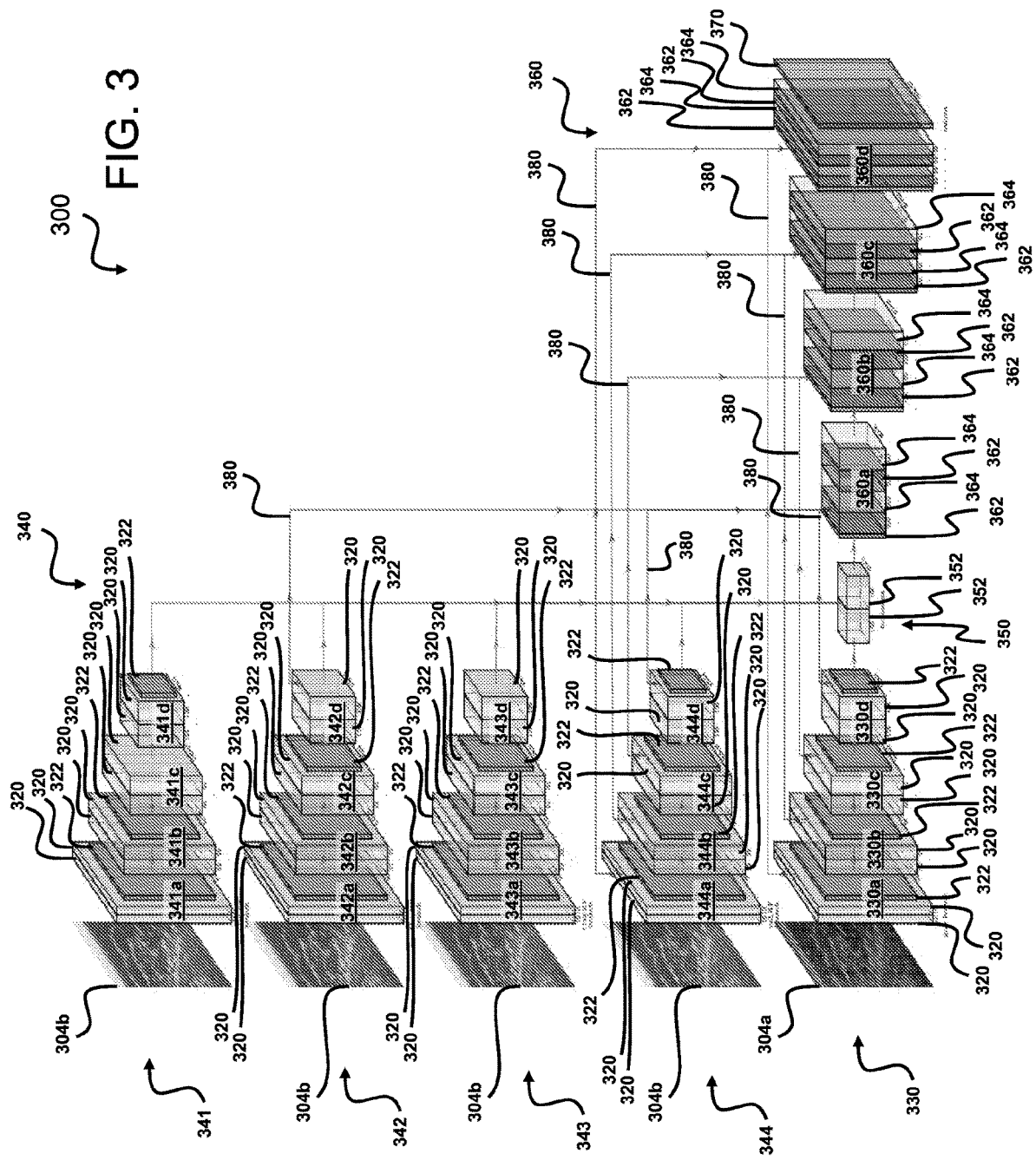
FIG. 3 illustrates an exemplary implementation of a convolutional neural network according to non-limiting embodiments or aspects.

Referring now to FIG. 3, an exemplary CNN 300 (e.g., W-Net CNN architecture) is shown according to non-limiting embodiments or aspects. For example, CNN 300 may be implemented (e.g., completely, partially, and/or the like) by computing device 106. Additionally or alternatively, CNN 300 may be implemented (e.g., completely, partially, and/or the like) by at least one other computing device and/or direct implementation in (e.g., digital and/or analog) circuitry, separate from or including computing device 106.

As shown in FIG. 3, CNN 300 may include downsampling layers (e.g., ultrasound image encoding branch 330, RF encoding branches 340 (e.g., first RF encoding branch 341, second RF encoding branch 342, third RF encoding branch 343, and/or fourth RF encoding branch 344), and/or the like), bottleneck section 350, upsampling layers (e.g., decoding branch 360 and/or the like), any combination thereof, and/or the like.

With continued reference to FIG. 3, ultrasound image encoding branch 330 may downsample an image input, e.g., ultrasound image 304a and/or the like. For example, ultrasound image 304a may include a plurality of pixels of a greyscale image of the ultrasound. Additionally or alternatively, the ultrasound image 304a may be colorized, may contain color Doppler overlays, any combination thereof, and/or the like. In non-limiting embodiments or aspects, ultrasound image encoding branch 330 may include a plurality of convolution blocks (e.g., first convolution block 330a, second convolution block 330b, third convolution block 330c, and/or fourth convolution block 330d). Each convolution block (e.g., 330a, 330b, 330c, and/or 330d) may include at least one convolution layer set 320. For example, each convolution block (e.g., 330a, 330b, 330c, and/or 330d) may include two convolution layer sets 320. In non-limiting embodiments or aspects, each convolution layer set 320 may include a convolution layer, a batch normalization layer, an activation layer, any combination thereof, and/or the like. Additionally or alternatively, each convolution block (e.g., 330a, 330b, 330c, and/or 330d) may include a max-pool layer 322. In non-limiting embodiments or aspects, each convolution layer set 320 of first convolution block 330a may have 16 feature maps. Additionally or alternatively, the dimensions of each convolution layer set 320 of first convolution block 330a may be based on the dimension of the input image (e.g., ultrasound image 304a, which may have dimensions of 784×192 and/or the like) and/or the number of feature maps (e.g., 16). For example, the dimensions of each convolution layer set 320 of first convolution block 330a may be 784×192×16. In non-limiting embodiments or aspects, each convolution layer set 320 of second convolution block 330b may have a greater number (e.g., double) of feature maps than those of first convolution block 330a (e.g., 32 feature maps), and/or the other dimensions of second convolution block 330b may be less than those of first convolution block 330a. For example, the dimensions of each convolution layer set 320 of second convolution block 330b may be 392×96×32. Additionally or alternatively, each convolution layer set 320 of third convolution block 330c may have a greater number (e.g., double) of feature maps than those of second convolution block 330b (e.g., 64 feature maps), and/or the other dimensions of third convolution block 330c may be less than those of second convolution block 330b. For example, the dimensions of each convolution layer set 320 of third convolution block 330c may be 196×48×64. Additionally or alternatively, each convolution layer set 320 of fourth convolution block 330d may have a greater number (e.g., double) of feature maps than those of third convolution block 330c (e.g., 128 feature maps), and/or the other dimensions of fourth convolution block 330d may be less than those of third convolution block 330c. For example, the dimensions of each convolution layer set 320 of fourth convolution block 330d may be 98×24×128. In non-limiting embodiments or aspects, the activation layer of each convolution layer set 320 in ultrasound image encoding branch 330 may include a rectified linear unit (ReLU) layer.

In non-limiting embodiments or aspects, at least some items of ultrasound data (e.g., ultrasound image 304a, RF waveform data 304b, labeled ultrasound images, and/or the like) may have different dimensions than others. For example, at least some items of ultrasound data may have dimensions of 592×192. In non-limiting embodiments or aspects, the architecture of CNN 300 may be limited to fixed-size input, and the items of ultrasound data having dimensions different than the fixed-size input (e.g., smaller in at least one dimension) may be zero-padded (e.g., at the bottom thereof) to match the input size. Additionally or alternatively, to reduce (e.g., minimize and/or the like) the introduction of phase artifacts when padding RF waveform data (e.g., RF images), RF images having dimensions different than the fixed-size input (e.g., smaller in at least one dimension) may be mirrored and/or reflected at the last (e.g., deepest) zero crossing of each A-scan/waveform to avoid waveform discontinuities and fill in padding values. In non-limiting embodiments or aspects, error metrics (e.g., for training and/or testing) may treat the padded region as a special-purpose background in the segmentation task and/or exclude the padded region from the loss function (e.g., while training CNN 300).

In non-limiting embodiments or aspects, the output of first convolution block 330a may be provided as input to second convolution block 330b. Additionally or alternatively, the output of second convolution block 330b may be provided as input to third convolution block 330c. Additionally or alternatively, the output of third convolution block 330c may be provided as input to fourth convolution block 330d. Additionally or alternatively, the output of fourth convolution block 330d may be provided as input to bottleneck section 350.

In FIG. 3, RF encoding branches 340 may include a plurality of RF encoding branches, e.g., first RF encoding branch 341, second RF encoding branch 342, third RF encoding branch 343, and/or fourth RF encoding branch 344. Additionally or alternatively, each RF encoding branch (e.g., 341, 342, 343, and/or 344) may downsample an RF input, e.g., RF waveform data 304b and/or the like. In non-limiting embodiments or aspects, each RF encoding branch (e.g., 341, 342, 343, and/or 344) may include a respective kernel size different than the other RF encoding branches. Additionally or alternatively, at least some of the kernels may be shaped and/or oriented to analyze a range of waveform values along single or small set of adjacent waveforms. For example, with the vertical A-scan waveforms of a linear probe, tall-thin rectangular kernels may be used. For example, the kernel size of first RF encoding branch 341 may be 51×9, the kernel size of second encoding branch 342 may be 21×5, the kernel size of third encoding branch 343 may be 11×3, and the kernel size of fourth encoding branch 344 may be 7×3.

In non-limiting embodiments or aspects, the respective kernel size of each RF encoding branch (e.g., 341, 342, 343, and/or 344) may correspond to a respective wavelength (e.g., of RF spectrum and/or the like). For example, due to different kernel sizes, RF encoding branches 340 may bin the RF waveform analysis into different frequency bands corresponding to the wavelength support of each branch, which may aid in segmentation (e.g., classification and/or the like). In non-limiting embodiments or aspects, the weights of at least some convolution blocks of the RF encoding branches (e.g., 341, 342, 343, and/or 344) may be initialized with local-frequency analysis kernels (e.g., wavelets, vertically oriented Gabor kernels, and/or the like), e.g., to encourage CNN 300 to learn appropriate Gabor kernels to better bin the RF input into various frequency bands. For example, initial Gabor filters may include spatial frequencies in the range [0.1, 0.85] with variance $\sigma_x \in [3, 5, 10, 25]$ and $\sigma_y \in [1, 2, 4]$, and such Gabor filters may have frequency separation of 3-8 MHz (which may be within the range of standard clinical practice, e.g., for portable point-of-care ultrasound (POCUS)). In non-limiting embodiments or aspects, the first two convolution blocks of each RF encoding branch may include kernels designed to hold a specific size of Gabor filter, e.g., sizes 7×3, 11×3, 21×5, and 51×9 (one per branch), as described herein. For example, the 11×3 Gabor filter may be embedded into a convolution kernel of size 21×5 (e.g., going out to two standard deviations instead of one). In non-limiting embodiments or aspects, kernel sizes (e.g., the aforementioned kernel sizes) may be chosen to allow connections 380 (e.g., residual connections, skip connections, and/or the like) into the decoding branch 360 (e.g., matching the output size of the ultrasound image encoding branch 330). In non-limiting embodiments or aspects, RF encoding branches with 11×3, 21×5, and 51×9 kernels may not have max-pooling (e.g., downsampling) layers 322 in the fourth, fourth, and third convolution blocks thereof, respectively, as described herein. For example, this omission of max-pooling (e.g., downsampling) layers 322 may compensate for losing input-image boundary pixels.

In non-limiting embodiments or aspects, each RF encoding branch (e.g., 341, 342, 343, and/or 344) may include a plurality of convolution blocks, e.g., a first convolution block (e.g., 341a, 342a, 343a, and/or 344a), a second convolution block (e.g., 341b, 342b, 343b, and/or 344b), a third convolution block (e.g., 341c, 342c, 343c, and/or 344c), and/or a fourth convolution block (e.g., 341d, 342d, 343d, and/or 344d). Each convolution block may include at least one convolution layer set 320 (e.g., two convolution layer sets 320) as described herein, and each convolution layer set 320 may include a convolution layer, a batch normalization layer, an activation layer, any combination thereof, and/or the like, as described herein. Additionally or alternatively, at least some convolution blocks (e.g., each convolution block, a subset of convolutions blocks, and/or the like) may include a max-pool layer 322, as described herein. For example, third convolution block 341c of first RF encoding branch 341, fourth convolution block 342d of second RF encoding branch 342, and/or fourth convolution block 343d of third RF encoding branch 343 may not include a max-pool layer 322, and/or the other convolution blocks of each RF encoding branch (e.g., 341, 342, 343, and/or 344) may each include a max-pool layer 322. In non-limiting embodiments or aspects, each convolution layer set 320 of the first convolution blocks (e.g., 341a, 342a, 343a, and/or 344a) may have 16 feature maps and/or the dimensions of each convolution layer set 320 of the first convolution block (e.g., 341a, 342a, 343a, and/or 344a) may be 784×192×16, as described herein. Additionally or alternatively, the dimensions of each convolution layer set 320 of the second convolution blocks (e.g., 341b, 342b, 343b, and/or 344b) may be 392×96×32, as described herein. Additionally or alternatively, the dimensions of each convolution layer set 320 of the third convolution blocks (e.g., 341c, 342c, 343c, and/or 344c) may be 196×48×64, as described herein. Additionally or alternatively, the dimensions of each convolution layer set 320 of the fourth convolution blocks (e.g., 341d, 342d, 343d, and/or 344d) may be 98×24×128, as described herein. In non-limiting embodiments or aspects, the activation layer of each convolution layer set 320 in RF encoding branches 340 may include a ReLU layer.

In non-limiting embodiments or aspects, the output of each respective first convolution block (e.g., 341*a*, 342*a*, 343*a*, and/or 344*a*) may be provided as input to each respective second convolution block (e.g., 341*b*, 342*b*, 343*b*, and/or 344*b*). Additionally or alternatively, the output of each respective second convolution block (e.g., 341*b*, 342*b*, 343*b*, and/or 344*b*) may be provided as input to each respective third convolution block (e.g., 341*c*, 342*c*, 343*c*, and/or 344*c*). Additionally or alternatively, the output of each respective third convolution block (e.g., 341*c*, 342*c*, 343*c*, and/or 344*c*) may be provided as input to each respective fourth convolution block (e.g., 341*d*, 342*d*, 343*d*, and/or 344*d*). Additionally or alternatively, the output of each respective fourth convolution block (e.g., 341*d*, 342*d*, 343*d*, and/or 344*d*) may be provided as input to bottleneck section 350.

As shown in FIG. 3, bottleneck section 350 may include at least one convolution layer set 352 (e.g., two convolution layer sets 352), as described herein. For example, each convolution layer set 352 may include a convolution layer, a batch normalization layer, an activation layer, any combination thereof, and/or the like, as described herein. In non-limiting embodiments or aspects, the activation layer of each convolution layer set 352 may include a ReLU layer. In non-limiting embodiments or aspects, each convolution layer set 352 may have a greater number (e.g., double) of feature maps than those of the fourth convolution blocks (e.g., 330*d*, 341*d*, 342*d*, 343*d*, and/or 344*d*) of the ultrasound image encoding branch 330 and/or RF encoding branches 340 (e.g., 768 feature maps), and/or the other dimensions of each convolution layer set 352 may be less than those of the fourth convolution blocks. For example, the dimensions of each convolution layer set 352 may be 49×12×768.

In non-limiting embodiments or aspects, the output of fourth convolution block 330*d* of ultrasound image encoding branch 330 and the output of each respective fourth convolution block (e.g., 341*d*, 342*d*, 343*d*, and/or 344*d*) of RF encoding branches 340 may be provided as input to bottleneck section 350. Additionally or alternatively, such outputs from the encoding branches may be combined (e.g., concatenated, aggregated, and/or the like) before being provided as input to bottleneck section 350.

In non-limiting embodiments or aspects, the output of bottleneck section 350 may be provided as input to decoding branch 360.

With continued reference to FIG. 3, decoding branch 360 may upsample the input thereto (e.g., the output from bottleneck section 350 and/or the like). In non-limiting embodiments or aspects, decoding branch 360 may include a plurality of up-convolution blocks (e.g., first up-convolution block 360*a*, second up-convolution block 360*b*, third up-convolution block 360*c*, and/or fourth up-convolution block 360*d*). Each up-convolution block (e.g., 360*a*, 360*b*, 360*c*, and/or 360*d*) may include at least one up-convolution layer 362 (e.g., a transposed convolution layer and/or the like) and/or at least one convolution layer set 364. For example, each up-convolution block (e.g., 360*a*, 360*b*, 360*c*, and/or 360*d*) may include two up-convolution layers 362 and/or two convolution layer sets 364 (e.g., in order, a first up-convolution layer 362, a first convolution layer set 364, a second up-convolution layer 362, and a second convolution layer set 364). In non-limiting embodiments or aspects, each convolution layer set 364 may include a convolution layer, a batch normalization layer, an activation layer, any combination thereof, and/or the like. In non-limiting embodiments or aspects, each up-convolution layer 362 and/or each convolution layer set 364 of first up-convolution block 360*a* may have 256 feature maps. Additionally or alternatively, the dimensions of each up-convolution layer 362 and/or each convolution layer set 364 of first up-convolution block 360*a* may be based on the dimensions of the input thereto (e.g., the output of bottleneck section 350 and/or the like), the dimensions of the fourth convolution block(s) of ultrasound image encoding branch 330 and/or RF encoding branches 340, and/or the number of feature maps (e.g., 256). For example, the dimensions of each up-convolution layer 362 and/or each convolution layer set 364 of first up-convolution block 360*a* may be 98×24×16. In non-limiting embodiments or aspects, each up-convolution layer 362 and/or each convolution layer set 364 of second up-convolution block 360*b* may have a lesser number (e.g., half) of feature maps than those of first up-convolution block 360*a* (e.g., 128 feature maps), and/or the other dimensions of second up-convolution block 360*b* may be based on the dimensions of the third convolution block(s) of ultrasound image encoding branch 330 and/or RF encoding branches 340. For example, the dimensions of each up-convolution layer 362 and/or each convolution layer set 364 of second up-convolution block 360*b* may be 196×48×128. Additionally or alternatively, each up-convolution layer 362 and/or each convolution layer set 364 of third up-convolution block 360*c* may have a lesser number (e.g., half) of feature maps than those of second up-convolution block 360*b* (e.g., 64 feature maps), and/or the other dimensions of third up-convolution block 360*c* may be based on the dimensions of the second convolution block(s) of ultrasound image encoding branch 330 and/or RF encoding branches 340. For example, the dimensions of each up-convolution layer 362 and/or each convolution layer set 364 of third up-convolution block 360*c* may be 392×96×64. Additionally or alternatively, each up-convolution layer 362 and/or each convolution layer set 364 of fourth up-convolution block 360*d* may have a lesser number (e.g., half) of feature maps than those of third up-convolution block 360*c* (e.g., 32 feature maps), and/or the other dimensions of fourth up-convolution block 360*d* may be based on the dimensions of the first convolution block(s) of ultrasound image encoding branch 330 and/or RF encoding branches 340. For example, the dimensions of each up-convolution layer 362 and/or each convolution layer set 364 of fourth up-convolution block 360*d* may be 784×192×32. In non-limiting embodiments or aspects, the activation layer of each convolution layer set 364 in decoding branch 360 may include a ReLU layer.

In non-limiting embodiments or aspects, the output of first up-convolution block 360*a* may be provided as input to second up-convolution block 360*b*. Additionally or alternatively, the output of second up-convolution block 360*b* may be provided as input to third up-convolution block 360*c*. Additionally or alternatively, the output of third up-convolution block 360*c* may be provided as input to fourth up-convolution block 360*d*. Additionally or alternatively, the output of fourth up-convolution block 360*d* may be provided as input to output layer set 370.

In non-limiting embodiments or aspects, the output layer set 370 may include at least one convolutional layer and/or at least one activation layer. In non-limiting embodiments or aspects, the activation layer of output layer set 370 may include a softmax layer. In non-limiting embodiments or aspects, the dimensions of the output layer set 370 may be based on the dimensions of fourth up-convolution block 360*d* of decoding branch 360 and/or the dimensions of the input ultrasound data (e.g., ultrasound image 304*a* and/or RF waveform data 304b). For example, the dimensions of the output layer set 370 may be 784×192. In non-limiting embodiments or aspects, the activation layer of output layer set 370 may include a classification layer. For example, the activation layer (e.g., classification layer) may assign a classification index (e.g., an integer class label and/or the like) to each pixel of the ultrasound to provide a semantic segmentation (e.g., a label map and/or the like). In non-limiting embodiments or aspects, the class label may be selected from the set {1, 2, 3, 4, 5}, where the following integers may correspond to the following types of tissue: (1) skin (e.g., epidermis/dermis], (2) fat, (3) fat fascia/stroma, (4) muscle, and (5) muscle fascia.

In non-limiting embodiments or aspects, CNN 300 may include a plurality of connections 380 (e.g., skip, residual, feed-forward, and/or the like connections). For example, each connection 380 may connect a respective convolution block (e.g., the output thereof) of the encoding branches (e.g., ultrasound image encoding branch 330 and/or RF encoding branches 340) to a respective up-convolution block (e.g., the input thereof) of the plurality of up-convolution blocks of decoding branch 360, which may have dimensions corresponding to the dimensions of the respective convolution block. In non-limiting embodiments or aspects, encoded feature data (e.g., the output of the respective convolution block) from such residual connections 380 may be concatenated with the input at the respective up-convolution block. In non-limiting embodiments or aspects, each convolution block may have a connection to the respective up-convolution block having corresponding (e.g., matching, compatible, and/or the like) dimensions thereto.

Referring now to FIG. 4, an exemplary CNN 400 (e.g., U-Net CNN architecture) is shown according to non-limiting embodiments or aspects. For example, CNN 400 may be implemented (e.g., completely, partially, and/or the like) by computing device 106. Additionally or alternatively, CNN 400 may be implemented (e.g., completely, partially, and/or the like) by at least one other computing device, separate from or including computing device 106.

As shown in FIG. 4, CNN 400 may include downsampling layers (e.g., encoding branch 430 and/or the like), bottleneck section 450, upsampling layers (e.g., decoding branch 460 and/or the like), any combination thereof, and/or the like.

With continued reference to FIG. 4, encoding branch 430 may downsample input ultrasound data 404. For example, ultrasound data 404 may include at least one ultrasound image, RF waveform data, any combination thereof, and/or the like, as described herein. In non-limiting embodiments or aspects, at least one ultrasound image (e.g., a single channel ultrasound image) may be combined with (e.g., concatenated with and/or the like) RF waveform data (e.g., a single-channel RF image) corresponding to the ultrasound image to form a multi-channel input image, e.g., for use as the input ultrasound data 404.

In non-limiting embodiments or aspects, encoding branch 430 may include a plurality of convolution blocks (e.g., first convolution block 430a, second convolution block 430b, third convolution block 430c, and/or fourth convolution block 430d). Each convolution block (e.g., 430a, 430b, 430c, and/or 430d) may include at least one convolution layer set 420. For example, each convolution block (e.g., 430a, 430b, 430c, and/or 430d) may include two convolution layer sets 420. In non-limiting embodiments or aspects, each convolution layer set 420 may include a convolution layer (e.g., a 3×3 convolution layer and/or the like), a batch normalization layer, an activation layer (e.g., a ReLU layer and/or the like), any combination thereof, and/or the like. Additionally or alternatively, each convolution block (e.g., 430a, 430b, 430c, and/or 430d) may include a max-pool layer 422 (e.g., a 2×2 max-pool layer and/or the like). In non-limiting embodiments or aspects, each convolution layer set 420 of first convolution block 430a may have 32 feature maps. Additionally or alternatively, the dimensions of each convolution layer set 420 of first convolution block 430a may be based on the dimension of the input image (e.g., ultrasound image and/or RF image, which may have dimensions of 784×192 and/or the like) and/or the number of feature maps (e.g., 64), as described herein. In non-limiting embodiments or aspects, each convolution layer set 420 of second convolution block 430b may have a greater (e.g., double) number of feature maps than those of first convolution block 430a (e.g., 64 feature maps), and/or the other dimensions of second convolution block 430b may be less than those of first convolution block 430a, as described herein. Additionally or alternatively, each convolution layer set 420 of third convolution block 430c may have a greater number (e.g., double) of feature maps than those of second convolution block 430b (e.g., 128 feature maps), and/or the other dimensions of third convolution block 430c may be less than those of second convolution block 430b, as described herein. Additionally or alternatively, each convolution layer set 420 of fourth convolution block 430d may have a greater number (e.g., double) of feature maps than those of third convolution block 430c (e.g., 256 feature maps), and/or the other dimensions of fourth convolution block 430d may be less than those of third convolution block 430c, as described herein. In non-limiting embodiments or aspects, the activation layer of each convolution layer set 420 in encoding branch 430 may include a ReLU layer.

In non-limiting embodiments or aspects, the output of first convolution block 430a may be provided as input to second convolution block 430b. Additionally or alternatively, the output of second convolution block 430b may be provided as input to third convolution block 430c. Additionally or alternatively, the output of third convolution block 430c may be provided as input to fourth convolution block 430d. Additionally or alternatively, the output of fourth convolution block 430d may be provided as input to bottleneck section 450.

As shown in FIG. 4, bottleneck section 450 may include at least one convolution layer set 452 (e.g., two convolution layer sets 452), as described herein. For example, each convolution layer set 452 may a convolution layer (e.g., a 3×3 convolution layer and/or the like), a batch normalization layer, an activation layer (e.g., a ReLU layer and/or the like), any combination thereof, and/or the like, as described herein. In non-limiting embodiments or aspects, the activation layer of each convolution layer set 452 may include a ReLU layer. In non-limiting embodiments or aspects, each convolution layer set 452 may have a greater number (e.g., double) of feature maps than those of fourth convolution block 403d (e.g., 512 feature maps), and/or the other dimensions of each convolution layer set 452 may be less than those of the fourth convolution blocks 430d, as described herein.

In non-limiting embodiments or aspects, the output of fourth convolution block 430d of encoding branch 430 may be provided as input to bottleneck section 450. Additionally or alternatively, the output of bottleneck section 450 may be provided as input to decoding branch 460.

With continued reference to FIG. 4, decoding branch 460 may upsample the input thereto (e.g., the output from bottleneck section 450 and/or the like). In non-limiting embodiments or aspects, decoding branch 460 may include a plurality of up-convolution blocks (e.g., first up-convolution block 460a, second up-convolution block 460b, third up-convolution block 460c, and/or fourth up-convolution block 460d). Each up-convolution block (e.g., 460a, 460b, 460c, and/or 460d) may include at least one up-convolution layer 462 (e.g., a transposed convolution layer and/or the like) and/or at least one convolution layer set 464. For example, each up-convolution block (e.g., 460a, 460b, 460c, and/or 460d) may include one up-convolution layer 462 and/or two convolution layer sets 464 (e.g., in order, up-convolution layer 462, a first convolution layer set 464, and a second convolution layer set 464). In non-limiting embodiments or aspects, each convolution layer set 464 may include a convolution layer (e.g., a 3×3 convolution layer and/or the like), a batch normalization layer, an activation layer (e.g., a ReLU layer and/or the like), any combination thereof, and/or the like. In non-limiting embodiments or aspects, each up-convolution layer 462 and/or each convolution layer set 464 of first up-convolution block 460a may have 256 feature maps, and/or the dimensions of each up-convolution layer 462 and/or each convolution layer set 464 of first up-convolution block 460a may be based on the dimensions of fourth convolution block 430d of encoding branch 430, as described herein. Additionally or alternatively, each up-convolution layer 462 and/or each convolution layer set 464 of second up-convolution block 460b may have a lesser number (e.g., half) of feature maps than those of first up-convolution block 460a (e.g., 128 feature maps), and/or the other dimensions of second up-convolution block 460b may be based on the dimensions of the third convolution block 430c of encoding branch 430. Additionally or alternatively, each up-convolution layer 462 and/or each convolution layer set 464 of third up-convolution block 460c may have a lesser number (e.g., half) of feature maps than those of second up-convolution block 460b (e.g., 64 feature maps), and/or the other dimensions of third up-convolution block 460c may be based on the dimensions of second convolution block 430b of encoding branch 430. Additionally or alternatively, each up-convolution layer 462 and/or each convolution layer set 464 of fourth up-convolution block 460d may have a lesser number (e.g., half) of feature maps than those of third up-convolution block 460c (e.g., 32 feature maps), and/or the other dimensions of fourth up-convolution block 460d may be based on the dimensions of first convolution block 430a of encoding branch 430.

In non-limiting embodiments or aspects, the output of first up-convolution block 460a may be provided as input to second up-convolution block 460b. Additionally or alternatively, the output of second up-convolution block 460b may be provided as input to third up-convolution block 460c. Additionally or alternatively, the output of third up-convolution block 460c may be provided as input to fourth up-convolution block 460d. Additionally or alternatively, the output of fourth up-convolution block 460d may be provided as input to output layer set 470.

In non-limiting embodiments or aspects, the output layer set 470 may include at least one convolutional layer and/or at least one activation layer. For example, the output layer set 470 may include a 1×1 convolutional layer and an activation layer (e.g., a softmax layer and/or the like). In non-limiting embodiments or aspects, the dimensions of the output layer set 470 may be based on the dimensions of fourth up-convolution block 460d of decoding branch 460 and/or the dimensions of the input ultrasound data (e.g., ultrasound image and/or RF image). For example, the dimensions of the output layer set 470 may be 784×192. In non-limiting embodiments or aspects, the activation layer of output layer set 470 may include a classification layer. For example, the activation layer (e.g., classification layer) may assign a classification index (e.g., an integer class label and/or the like) to each pixel of the ultrasound to provide a semantic segmentation (e.g., a label map and/or the like).

In non-limiting embodiments or aspects, CNN 400 may include a plurality of feature-forwarding connections 480 (e.g., skip connections, residual connections, and/or the like). For example, each residual connection 480 may connect a respective convolution block (e.g., the output thereof) of encoding branch 430 to a respective up-convolution block (e.g., the input thereof) of decoding branch 460, which may have dimensions corresponding to the dimensions of the respective convolution block. In non-limiting embodiments or aspects, encoded feature data (e.g., the output of the respective convolution block) from such residual connections 480 may be concatenated with the input at the respective up-convolution block.

In non-limiting embodiments or aspects, the classification output of CNN 400 may be optimized during training. For example, cross-entropy loss may be used prior to the activation layer of the output layer set 470 (e.g., the final softmax layer and/or the like) as the objective function to train CNN 400 to seek large numerical separations for each pixel between the max (e.g., final output) scores versus the non-max responses for the other classes (e.g., which may create a more robust, more generalized CNN).

In non-limiting embodiments or aspects, CNN 400 may be similar to the CNN described in Ronneberger et al., U-net: Convolutional networks for biomedical image segmentation, International Conference on Medical Image Computing and Computer-Assisted Intervention, 234-241 (2015), the disclosure of which is incorporated by reference herein in its entirety.

Referring now to FIG. 5, an exemplary CNN 500 (e.g., SegNet CNN architecture) is shown according to non-limiting embodiments or aspects. For example, CNN 500 may be implemented (e.g., completely, partially, and/or the like) by computing device 106. Additionally or alternatively, CNN 500 may be implemented (e.g., completely, partially, and/or the like) by at least one other computing device, separate from or including computing device 106.

As shown in FIG. 5, CNN 500 may include downsampling layers (e.g., encoding branch 530 and/or the like), upsampling layers (e.g., decoding branch 560 and/or the like), any combination thereof, and/or the like.

With continued reference to FIG. 5, encoding branch 530 may downsample input ultrasound data. For example, ultrasound data may include at least one ultrasound image, RF waveform data, any combination thereof, and/or the like, as described herein. In non-limiting embodiments or aspects, at least one ultrasound image (e.g., a single channel ultrasound image) may be combined with (e.g., concatenated with and/or the like) RF waveform data (e.g., a single-channel RF image) corresponding to the ultrasound image to form a multi-channel input image, e.g., for use as the input ultrasound data.

In non-limiting embodiments or aspects, encoding branch 530 may include a plurality of convolution blocks (e.g., first convolution block 530a, second convolution block 530b, third convolution block 530c, fourth convolution block 530d, and/or fifth convolution block 530e). Each convolution block (e.g., 530a, 530b, 530c, 530d, and/or 530e) may include at least one convolution layer set 520. For example, each convolution block (e.g., 530a, 530b, 530c, and/or 530d) may include two or three convolution layer sets 520

(e.g., first convolution block 530*a* and second convolution block 530*b* may each include two convolution layer sets 520, and third convolution block 530*c*, fourth convolution block 530*d*, and fifth convolution block 530*e* may each include three convolution layer sets 520). In non-limiting embodiments or aspects, each convolution layer set 520 may include a convolution layer, a batch normalization layer, an activation layer (e.g., a ReLU layer and/or the like), any combination thereof, and/or the like. Additionally or alternatively, each convolution block (e.g., 530*a*, 530*b*, 530*c*, 530*d*, and/or 530*e*) may include a pooling layer 522 (e.g., a max-pool layer and/or the like).

In non-limiting embodiments or aspects, the output of first convolution block 530*a* may be provided as input to second convolution block 530*b*. Additionally or alternatively, the output of second convolution block 530*b* may be provided as input to third convolution block 530*c*. Additionally or alternatively, the output of third convolution block 530*c* may be provided as input to fourth convolution block 530*d*. Additionally or alternatively, the output of fourth convolution block 530*d* may be provided as input to fifth convolution block 530*e*. Additionally or alternatively, the output of fifth convolution block 530*e* may be provided as input to decoding branch 560.

With continued reference to FIG. 5, decoding branch 560 may upsample the input thereto (e.g., the output from encoding branch 530 and/or the like). In non-limiting embodiments or aspects, decoding branch 560 may include a plurality of upsampling blocks (e.g., first upsampling block 560*a*, second upsampling block 560*b*, third upsampling block 560*c*, fourth upsampling block 560*d*, and/or fifth upsampling block 560*e*). Each upsampling block (e.g., 560*a*, 560*b*, 560*c*, 560*d*, and/or 560*e*) may include at least one upsampling layer 562 and/or at least one convolution layer set 564. For example, each upsampling block (e.g., 560*a*, 560*b*, 560*c*, 560*d*, and/or 560*e*) may include one upsampling layer 562 and two or three convolution layer sets 564 (e.g., first upsampling block 560*a*, second upsampling block 560*b*, and third upsampling block 560*c* may each include three convolution layer sets 564, and fourth upsampling block 560*d* and fifth upsampling block 560*e* may each include three convolution layer sets 520). In non-limiting embodiments or aspects, each upsampling layer may use max-pooling indices captured and stored in encoding branch 530 step to upsample the input thereto. In non-limiting embodiments or aspects, each convolution layer set 564 may include a convolution layer, a batch normalization layer, an activation layer (e.g., a ReLU layer and/or the like), any combination thereof, and/or the like.

In non-limiting embodiments or aspects, the output of first upsampling block 560*a* may be provided as input to second upsampling block 560*b*. Additionally or alternatively, the output of second upsampling block 560*b* may be provided as input to third upsampling block 560*c*. Additionally or alternatively, the output of third upsampling block 560*c* may be provided as input to fourth upsampling block 560*d*. Additionally or alternatively, the output of fourth upsampling block 560*d* may be provided as input to fifth upsampling block 560*e*. Additionally or alternatively, the output of fifth upsampling block 560*e* may be provided as input to output layer set 570.

In non-limiting embodiments or aspects, the output layer set 570 may include at least one activation layer. For example, the activation layer may include a softmax layer. In non-limiting embodiments or aspects, the dimensions of the output layer set 570 may be based on the dimensions of the input ultrasound data (e.g., ultrasound image and/or RF image). For example, the dimensions of the output layer set 570 may be 784×192. In non-limiting embodiments or aspects, the activation layer of output layer set 570 may include a classification layer. For example, the activation layer (e.g., classification layer) may assign a classification index (e.g., an integer class label and/or the like) to each pixel of the ultrasound to provide a semantic segmentation (e.g., a label map and/or the like).

In non-limiting embodiments or aspects, CNN 500 may include a plurality of feature forwarding connections 580 (e.g., skip connections, residual connections, and/or the like). For example, each connection 580 may connect a respective convolution block (e.g., the output thereof) of encoding branch 530 to a respective upsampling block (e.g., the input thereof) of decoding branch 560, which may have dimensions corresponding to the dimensions of the respective convolution block. In non-limiting embodiments or aspects, encoded feature data (e.g., the output of the respective convolution block) from such residual connections 580 may be concatenated with the input at the respective upsampling block.

In non-limiting embodiments or aspects, CNN 500 may be similar to the CNN described in Badrinarayanan et al., Segnet A Deep Convolutional Encoder-Decoder Architecture for Image Segmentation, 39 IEEE Transactions on Pattern Analysis and Machine Intelligence, 2481-2495 (2017), the disclosure of which is incorporated by reference herein in its entirety.

Figure 6A:
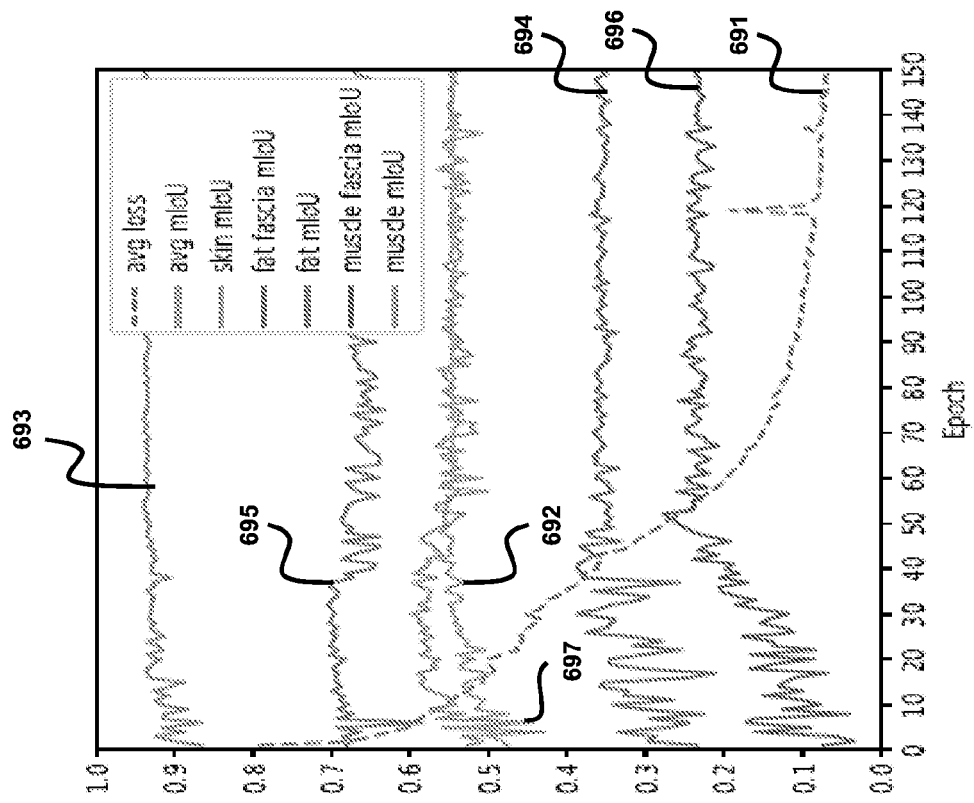
FIGS. 6A-6C show test data of results of implementations according to non-limiting embodiments or aspects.

Referring now to FIG. 6A, shown is a graph of average loss and mean intersection over union (mIoU) metrics for various tissue classes versus training epochs for an exemplary CNN 300 of FIG. 3 according to non-limiting embodiments or aspects. First curve 691 shows an example of the loss function value, averaged over tissue types, as it generally improves (gets smaller) in the course of training CNN 300. Second curve 692 shows an example of the mIoU metric value, averaged over tissue types, as it generally improves (gets closer to 1.0) in the course of training CNN. Third curve 693 shows an example of the mIoU of CNN 300 for segmenting skin tissue as it generally improves in the course of training. Fourth curve 694 shows an example of the mIoU of CNN 300 for segmenting fat fascia tissue as it generally improves in the course of training. Fifth curve 695 shows an example of the mIoU of CNN 300 for segmenting fat tissue as it generally improves during initial training (in this particular example, fat mIoU 395 eventually gets somewhat worse as fat fascia/stroma mIoU 394 improves). Sixth curve 696 shows an example of the mIoU of CNN 300 for segmenting muscle fascia tissue as it generally improves in the course of training. Seventh curve 697 shows an example of the mIoU of CNN 300 for segmenting muscle tissue as it generally improves during initial training (in this particular example, muscle mIoU 397 eventually gets somewhat worse as muscle fascia mIoU 396 improves). Each of these examples is illustrative, and individual training sessions will be expected to have different values/curves for each of these.

Figure 6B:
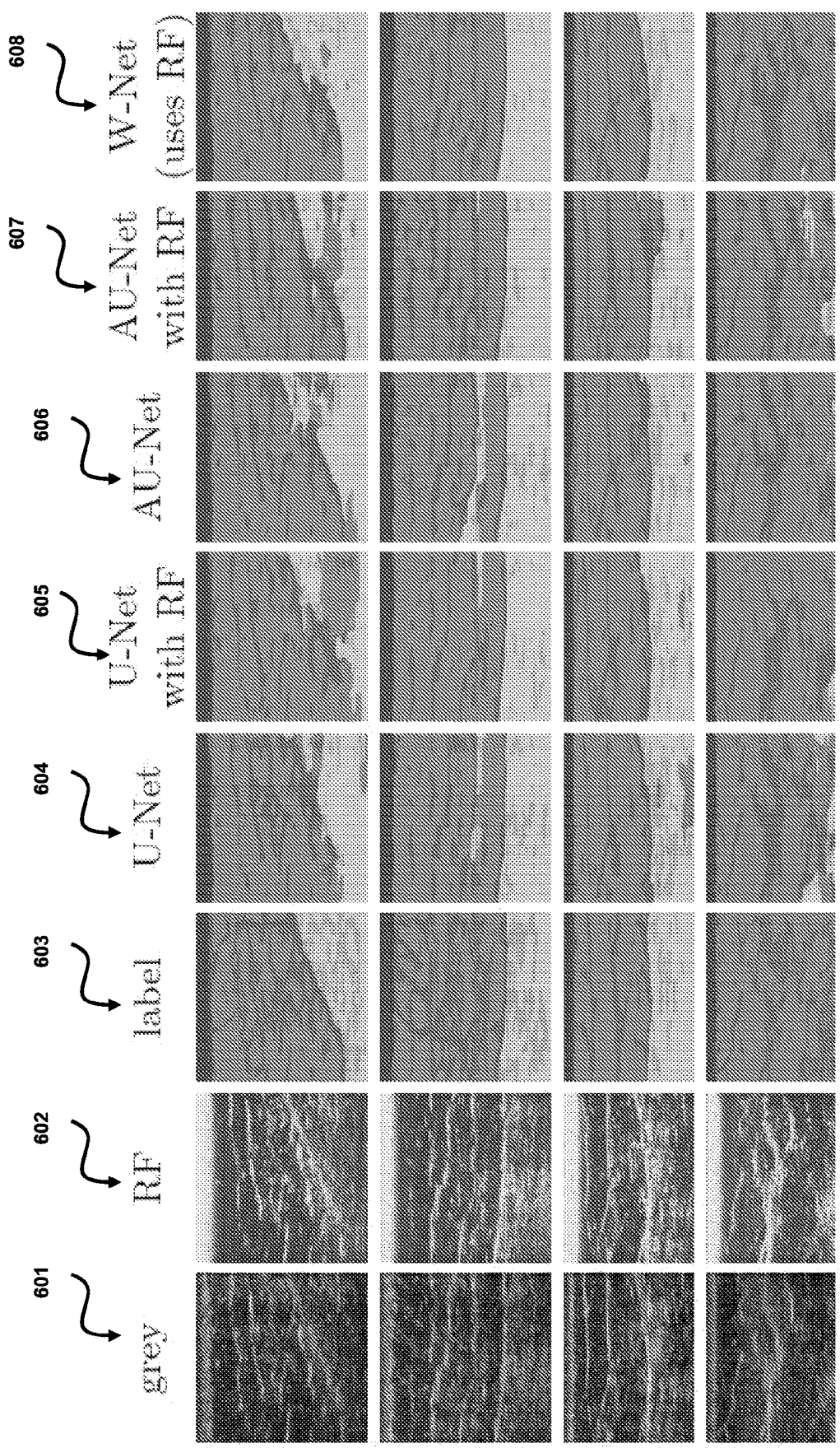

Referring now to FIG. 6B, shown are exemplary testing input images, corresponding labeled images, and output segmented ultrasound images for various exemplary CNNs according to non-limiting embodiments or aspects. First column 601 shows four exemplary ultrasound images (e.g., testing input ultrasound images), and second column 602 shows four exemplary RF images (e.g., testing input RF images, displayed using a color map to show both positive and negative waveform values) corresponding to the ultrasound images, respectively. Third column 603 shows four exemplary labeled images (e.g., labeled by a clinician and/or the like based respectively on the four exemplary ultrasound images and/or RF images). Fourth column 604 shows four exemplary output segmented ultrasound images from an exemplary CNN with U-Net architecture based on the four ultrasound images (e.g., without using the four RF images), respectively, and fifth column 605 shows four exemplary output segmented ultrasound images from an exemplary CNN with U-Net architecture based on the four ultrasound images and the four RF images, respectively. Sixth column 604 shows four exemplary output segmented ultrasound images from an exemplary CNN with Attention U-Net (AU-Net) architecture (e.g., the same as or similar to the CNN architecture described in Oktay et al., Attention U-Net Learning Where to Look for the Pancreas, 1st Conference on Medical Imaging with Deep Learning (MIDL) (2018), the disclosure of which is incorporated by reference herein in its entirety) based on the four ultrasound images (e.g., without using the four RF images), respectively, and seventh column 607 shows four exemplary output segmented ultrasound images from an exemplary CNN with AU-Net architecture based on the four ultrasound images and the four RF images, respectively. Eighth column 608 shows four exemplary output segmented ultrasound images from an exemplary CNN with W-Net architecture based on the four ultrasound images and the four RF images, respectively.

For the purpose of illustration, Table 1 shows an example of pixel-wise accuracy and mIoU of various exemplary input ultrasound images), and second row 612 shows five exemplary RF images (e.g., testing input RF images, displayed using a color map to show both positive and negative waveform values) corresponding to the ultrasound images, respectively. Third row 613 shows five exemplary labeled images (e.g., labeled by a clinician and/or the like based respectively on the five exemplary ultrasound images and/or RF images). Fourth row 614 shows five exemplary output segmented ultrasound images from an exemplary CNN with U-Net architecture based on the five ultrasound images (e.g., without using the five RF images), respectively, and fifth row 615 shows five exemplary output segmented ultrasound images from an exemplary CNN with SegNet architecture based on the five ultrasound images (e.g., without using the five RF images), respectively. Sixth row 616 shows five exemplary output segmented ultrasound images from an exemplary CNN with U-Net architecture based on the five ultrasound images and the five RF images, respectively, and seventh row 617 shows five exemplary output segmented ultrasound images from an exemplary CNN with SegNet architecture based on the five ultrasound images and the five RF images, respectively.

For the purpose of illustration, Table 2 shows an example of pixel-wise accuracy and mIoU of various exemplary CNNs (due to the random nature of training, slightly different and/or more diverging values may be expected from different training sessions):

TABLE 2

| CNN | Input data | Pixel-wise Acc. | mIoU |  |  |  |  |  |
|---|---|---|---|---|---|---|---|---|
|  |  |  | Mean | Skin | Fat fascia | Fat | Muscle fascia | Muscle |
| U-Net | Image only | 0.71788 | 0.53903 | 0.94903 | 0.47354 | 0.64848 | 0.20908 | 0.41502 |
| SegNet | Image only | 0.67951 | 0.52563 | 0.94131 | 0.37334 | 0.61568 | 0.24823 | 0.44957 |
| U-Net | Image + RF | 0.71273 | 0.54321 | 0.93611 | 0.40924 | 0.64085 | 0.27155 | 0.45835 |
| SegNet | Image + RF | 0.66912 | 0.49966 | 0.89674 | 0.36769 | 0.61828 | 0.18821 | 0.42737 |

CNNs (due to the random nature of training, slightly different and/or more diverging values may be expected from different training sessions):

TABLE 1

| CNN | Input data | Pixel-wise Acc. | mIoU |  |  |  |  |  |
|---|---|---|---|---|---|---|---|---|
|  |  |  | Mean | Skin | Fat fascia | Fat | Muscle fascia | Muscle |
| U-Net | Image only | 0.746 | 0.555 | 0.923 | 0.361 | 0.699 | 0.186 | 0.605 |
| U-Net | Image + RF | 0.755 | 0.565 | 0.926 | 0.357 | 0.706 | 0.179 | 0.657 |
| AU-Net | Image only | 0.741 | 0.553 | 0.924 | 0.371 | 0.689 | 0.181 | 0.601 |
| AU-Net | Image + RF | 0.740 | 0.555 | 0.927 | 0.355 | 0.688 | 0.179 | 0.627 |
| W-Net | Image + RF | 0.769 | 0.580 | 0.925 | 0.373 | 0.722 | 0.210 | 0.669 |

Figure 6C:
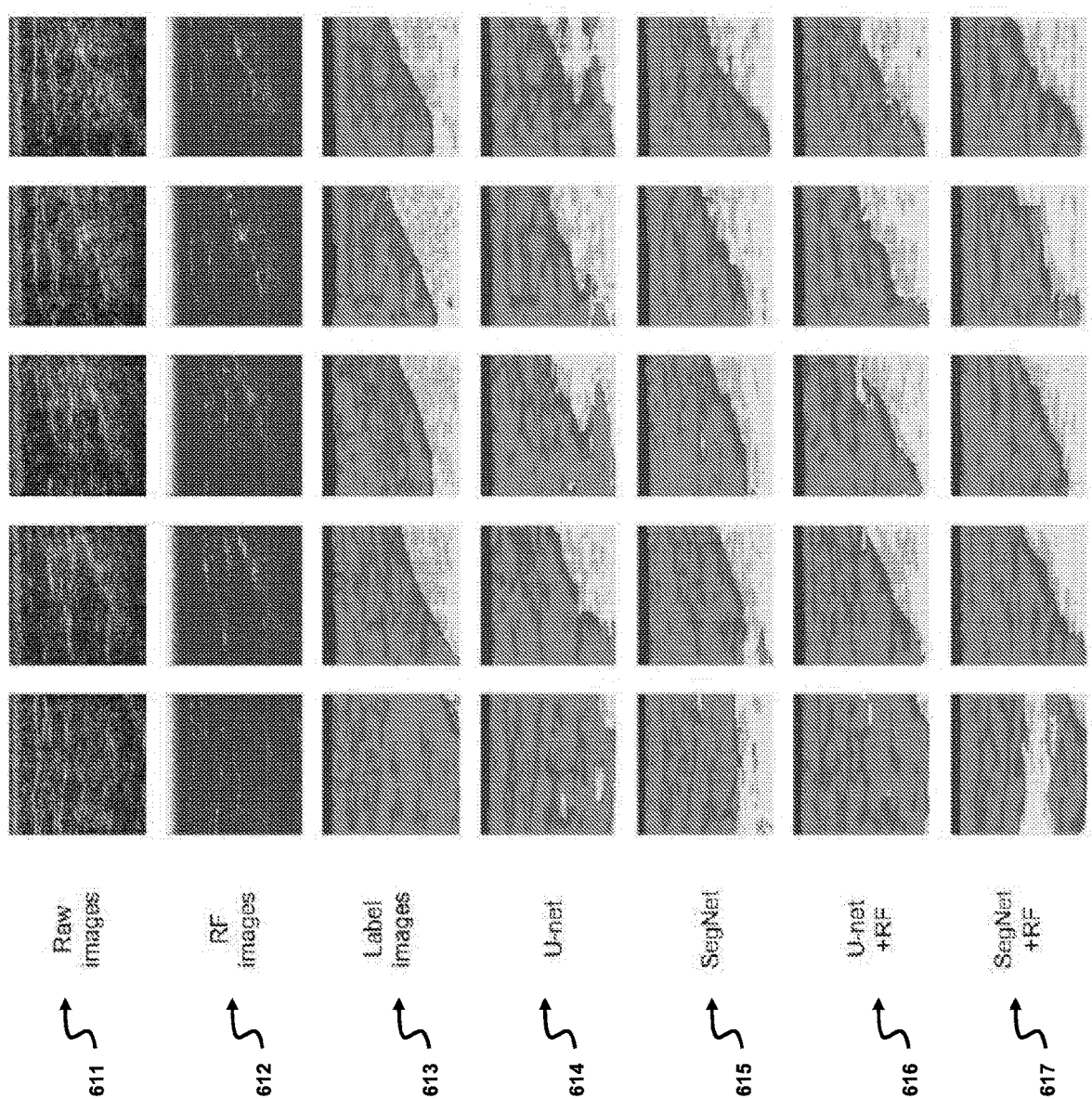

Referring now to FIG. 6C, shown are exemplary testing input images, corresponding labeled images, and output segmented ultrasound images for various exemplary CNNs according to non-limiting embodiments or aspects. First row 611 shows five exemplary ultrasound images (e.g., testing Referring now to FIG. 7, shown is a method 700 for labeling ultrasound data according to non-limiting embodiments. It will be appreciated that the order of the steps shown in FIG. 7 is for illustration purposes only and that non-limiting embodiments may involve more steps, fewer steps, different steps, and/or a different order of steps. Moreover, the example shown in FIG. 7 relates to ultrasound data but, as explained herein, the systems and methods disclosed herein may be used in many other contexts. In non-limiting embodiments or aspects, one or more of the steps of method 700 may be performed (e.g., completely, partially, and/or the like) by computing device 106. In non-limiting embodiments or aspects, one or more of the steps of method 700 may be performed (e.g., completely, partially, and/or the like) by another system, another device, another group of systems, or another group of devices, separate from or including computing device 106, such as ultrasound/RF system 102, at least one other computing device, and/or the like.

As shown in FIG. 7, at step 702, method 700 may include training a CNN, as described herein. For example, computing device 106 may train a CNN (e.g., W-Net, U-Net, AU-Net, SegNet, any combination thereof, and/or the like) based on ultrasound data 104, which may include at least one ultrasound image 104a, RF waveform data 104b (e.g., at least one RF image), any combination thereof, and/or the like. In non-limiting embodiments or aspects, computing device 106 may receive (e.g., retrieve, request, obtain, and/or the like) ultrasound data for training the CNN from at least one of ultrasound/RF system 102 and/or database 108. For example, computing device 106 may train the CNN based on historical ultrasound data (e.g., historical ultrasound image(s) 104a, RF waveform data 104b, labeled ultrasound images 104c, any combination thereof, and/or the like) from database 108, as described herein.

As shown in FIG. 7, at step 704, method 700 may include downsampling an RF input (e.g., RF waveform data 104b and/or the like) of each downsampling layer of a plurality of downsampling layers in the CNN, as described herein. For example, computing device 106 may downsample the RF input of the downsampling layers (e.g., encoding branch(es), RF encoding branch(es) and/or the like, as described herein). In non-limiting embodiments or aspects, the RF input may include RF waveform data 104b for an ultrasound received from at least one of ultrasound/RF system 102 and/or database 108, as described herein.

As shown in FIG. 7, at step 706, method 700 may include downsampling an image input (e.g., ultrasound image(s) 104a and/or the like) of each downsampling layer of a plurality of downsampling layers in the CNN, as described herein. For example, computing device 106 may downsample the image input of the downsampling layers (e.g., encoding branch(es), ultrasound image encoding branch(es) and/or the like, as described herein). In non-limiting embodiments or aspects, the image input may include at least one ultrasound image 104a for an ultrasound received from at least one of ultrasound/RF system 102 and/or database 108, as described herein. Additionally or alternatively, the image input may include a plurality of pixels of the ultrasound, as described herein.

In non-limiting embodiments or aspects, the image inputs and the RF inputs are processed substantially simultaneously, as described herein.

As shown in FIG. 7, at step 706, method 700 may include segmenting tissues in the ultrasound based on an output of the CNN, as described herein. For example, computing device 106 may segment tissues (e.g., label pixels identified therewith) in the ultrasound based on an output of the CNN, as described herein. In non-limiting embodiments or aspects, segmenting tissues in the ultrasound may include labeling a plurality of (e.g., a majority of, all of, and/or the like) pixels in the ultrasound, as described herein. In non-limiting embodiments or aspects, segmenting tissues may include identifying at least one of the following: muscle, fascia, fat fascia, muscle fascia, fat, grafted fat, any combination thereof, and/or the like, as described herein.

Figure 8:
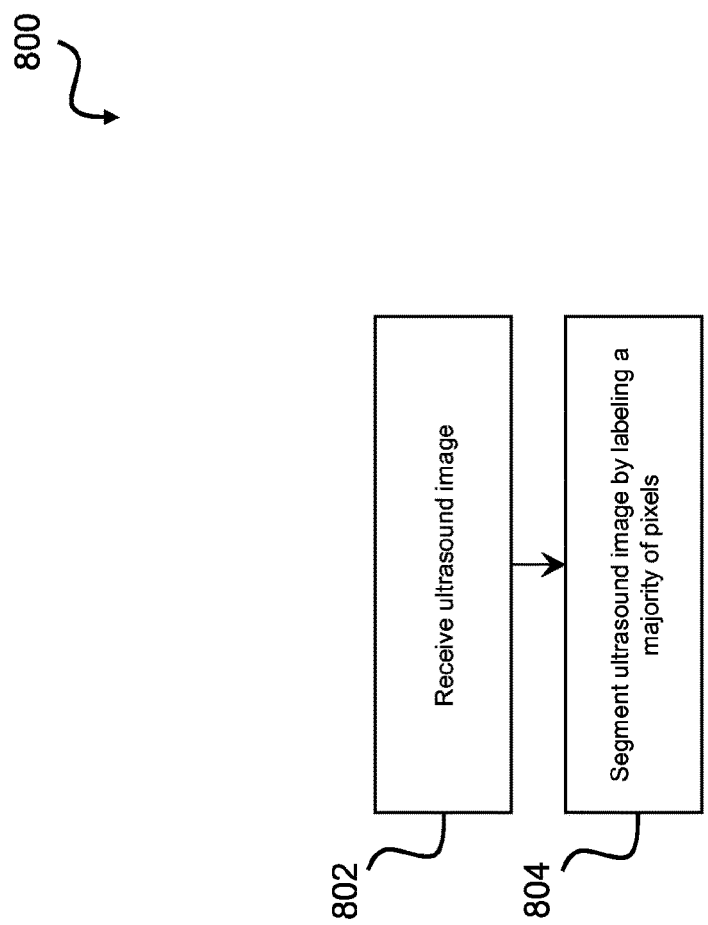
FIG. 8 is a flow diagram of a method for labeling ultrasound data according to non-limiting embodiments or aspects.

Referring now to FIG. 8, shown is a method 800 for labeling ultrasound data according to non-limiting embodiments. It will be appreciated that the order of the steps shown in FIG. 8 is for illustration purposes only and that non-limiting embodiments may involve more steps, fewer steps, different steps, and/or a different order of steps. Moreover, the example shown in FIG. 8 relates to ultrasound data but, as explained herein, the systems and methods disclosed herein may be used in many other contexts. In non-limiting embodiments or aspects, one or more of the steps of method 800 may be performed (e.g., completely, partially, and/or the like) by computing device 106. In non-limiting embodiments or aspects, one or more of the steps of method 800 may be performed (e.g., completely, partially, and/or the like) by another system, another device, another group of systems, or another group of devices, separate from or including computing device 106, such as ultrasound/RF system 102, at least one other computing device, and/or the like.

As shown in FIG. 8, at step 802, method 800 may include receiving an ultrasound image represented by a plurality of pixels. For example, computing device 106 may receive ultrasound image 104a from at least one of ultrasound/RF system 102 and/or database 108, as described herein.

As shown in FIG. 8, at step 804, method 800 may include segmenting the ultrasound image by labeling a majority of pixels of the plurality of pixels. For example, computing device 106 may segment ultrasound image 104a by labeling a majority of pixels thereof, as described herein. In non-limiting embodiments or aspects, the majority of pixels may be labeled as at least one of the following: muscle, fascia, fat fascia, muscle fascia, fat, grafted fat, any combination thereof, and/or the like, as described herein. In non-limiting embodiments or aspects, computing device 106 may segment ultrasound image 104a based on a CNN (e.g., the output thereof generated based on using ultrasound image 104a as input), as described herein. In non-limiting embodiments or aspect, computing device 106 may train the CNN based on ultrasound data 104 (e.g., historical ultrasound data from database 108, ultrasound image 104a received from ultrasound/RF system 102, and/or the like), as described herein. Additionally or alternatively, at least one input ultrasound image (e.g., labeled ultrasound image 104c and/or the like) in the ultrasound data 104 may include fuzzy overlapping labels for a plurality of pixels.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A method for labeling ultrasound data, comprising:
training a convolutional neural network (CNN) based on ultrasound data, the ultrasound data comprising radio frequency (RF) waveform data;
downsampling an RF input of each downsampling layer of a plurality of downsampling layers in the CNN, the RF input comprising RF waveform data for an ultrasound; and
segmenting tissues in the ultrasound based on an output of the CNN,
wherein the plurality of downsampling layers comprises an ultrasound image encoding branch and a plurality of RF encoding branches, each RF encoding branch comprising a respective kernel size different than other RF encoding branches of the plurality of RF encoding branches, the respective kernel size of each RF encoding branch corresponding to a respective wavelength,
wherein each RF encoding branch comprises a plurality of convolution blocks, each convolution block comprising a first convolution layer, a first batch normalization layer, a first activation layer, a second convolution layer, a second batch normalization layer, and a second activation layer, and at least one convolution block of the plurality of convolution blocks comprises a max-pooling layer, and wherein downsampling comprises downsampling the RF input of each RF encoding branch of the plurality of RF encoding branches in the CNN and downsampling an image input of each ultrasound image encoding branch in the CNN, the image input comprising a plurality of pixels of the ultrasound.

2. The method of claim 1, wherein the image input and the RF input are processed substantially simultaneously.

3. The method of claim 1, wherein segmenting tissues in the ultrasound comprises labeling a plurality of pixels.

4. The method of claim 3, wherein the plurality of pixels comprises a majority of pixels in the ultrasound.

5. The method of claim 1, wherein segmenting tissues comprises identifying at least one of the following: muscle, fascia, fat, grafted fat, or any combination thereof.

6. The method of claim 1, further comprising:
concatenating an RF encoding branch output of each RF encoding branch and an ultrasound image encoding branch output of the ultrasound image encoding branch to provide a concatenated encoding branch output; and
upsampling the concatenated encoding branch output with a plurality of upsampling layers in the CNN.

7. The method of claim 6, wherein the plurality of upsampling layers comprises a decoding branch, the decoding branch comprising a plurality of up-convolution blocks, wherein the CNN further comprises a plurality of residual connections, each residual connection connecting a respective convolution block of the plurality of convolution blocks to a respective up-convolution block of the plurality of up-convolution blocks having dimensions corresponding to the respective convolution block.

8. The method of claim 1, wherein a majority of pixels of the ultrasound are labeled during segmentation as at least one of the following: muscle, fascia, fat, grafted fat, or any combination thereof.

9. The method of claim 1, wherein at least one input ultrasound image in the ultrasound data comprises fuzzy overlapping labels for a plurality of pixels.

10. A system for labeling ultrasound data, comprising at least one computing device programmed or configured to:
train a convolutional neural network (CNN) based on ultrasound data, the ultrasound data comprising radio frequency (RF) waveform data;
downsample an RF input of each downsampling layer of a plurality of downsampling layers in the CNN, the RF input comprising RF waveform data for an ultrasound; and
segment tissues in the ultrasound based on an output of the CNN,
wherein the plurality of downsampling layers comprises an ultrasound image encoding branch and a plurality of RF encoding branches, each RF encoding branch comprising a respective kernel size different than other RF encoding branches of the plurality of RF encoding branches, the respective kernel size of each RF encoding branch corresponding to a respective wavelength,
wherein each RF encoding branch comprises a plurality of convolution blocks, each convolution block comprising a first convolution layer, a first batch normalization layer, a first activation layer, a second convolution layer, a second batch normalization layer, and a second activation layer, and at least one convolution block of the plurality of convolution blocks comprises a max-pooling layer, and
wherein downsampling comprises downsampling the RF input of each RF encoding branch of the plurality of RF encoding branches in the CNN and downsampling an image input of each ultrasound image encoding branch in the CNN, the image input comprising a plurality of pixels of the ultrasound.

11. The system of claim 10, wherein the image input and the RF input are processed substantially simultaneously.

12. The system of claim 10, wherein segmenting tissues in the ultrasound comprises labeling a plurality of pixels.

13. The system of claim 12, wherein the plurality of pixels comprises a majority of pixels in the ultrasound.

14. The system of claim 10, wherein segmenting tissues comprises identifying at least one of the following: muscle, fascia, fat, grafted fat, or any combination thereof.

15. The system of claim 10, wherein the at least one computing device is further programmed or configured to:
concatenate an RF encoding branch output of each RF encoding branch and an ultrasound image encoding branch output of the ultrasound image encoding branch to provide a concatenated encoding branch output; and
upsample the concatenated encoding branch output with a plurality of upsampling layers in the CNN.

16. The system of claim 15, wherein the plurality of upsampling layers comprises a decoding branch, the decoding branch comprising a plurality of up-convolution blocks, wherein the CNN further comprises a plurality of residual connections, each residual connection connecting a respective convolution block of the plurality of convolution blocks to a respective up-convolution block of the plurality of up-convolution blocks having dimensions corresponding to the respective convolution block.

17. A computer program product for labeling ultrasound data, comprising at least one non-transitory computer-readable medium including program instructions that, when executed by a computing device, cause the computing device to:
train a convolutional neural network (CNN) based on ultrasound data, the ultrasound data comprising radio frequency (RF) waveform data;
downsample an RF input of each downsampling layer of a plurality of downsampling layers in the CNN, the RF input comprising RF waveform data for an ultrasound; and
segment tissues in the ultrasound based on an output of the CNN,
wherein the plurality of downsampling layers comprises an ultrasound image encoding branch and a plurality of RF encoding branches, each RF encoding branch comprising a respective kernel size different than other RF encoding branches of the plurality of RF encoding branches, the respective kernel size of each RF encoding branch corresponding to a respective wavelength,
wherein each RF encoding branch comprises a plurality of convolution blocks, each convolution block comprising a first convolution layer, a first batch normalization layer, a first activation layer, a second convolution layer, a second batch normalization layer, and a second activation layer, and at least one convolution block of the plurality of convolution blocks comprises a max-pooling layer, and
wherein downsampling comprises downsampling the RF input of each RF encoding branch of the plurality of RF encoding branches in the CNN and downsampling an image input of each ultrasound image encoding branch in the CNN, the image input comprising a plurality of pixels of the ultrasound.

* * * * *